(12) United States Patent
Bundock

(10) Patent No.: US 12,215,363 B2
(45) Date of Patent: Feb. 4, 2025

(54) BALANCED INDELS

(71) Applicant: Keygene N.V., Wageningen (NL)

(72) Inventor: Paul Bundock, Wageningen (NL)

(73) Assignee: KEYGENE N.V., Wageningen (NL)

( * ) Notice: Subject to any disclaimer, the term of this patent is extended or adjusted under 35 U.S.C. 154(b) by 36 days.

(21) Appl. No.: 16/811,393

(22) Filed: Mar. 6, 2020

(65) Prior Publication Data

US 2020/0270626 A1    Aug. 27, 2020

Related U.S. Application Data

(63) Continuation of application No. PCT/EP2018/074150, filed on Sep. 7, 2018.

(30) Foreign Application Priority Data

Sep. 8, 2017   (EP) .................... 17190057

(51) Int. Cl.
| | | |
|---|---|---|
| C12N 9/22 | (2006.01) | |
| C12N 15/10 | (2006.01) | |
| C12N 15/82 | (2006.01) | |
| C12N 15/90 | (2006.01) | |

(52) U.S. Cl.
CPC ............ *C12N 9/22* (2013.01); *C12N 15/102* (2013.01); *C12N 15/8213* (2013.01); *C12N 15/8274* (2013.01); *C12N 15/90* (2013.01); *C12N 2310/20* (2017.05); *C12N 2800/22* (2013.01)

(58) Field of Classification Search
None
See application file for complete search history.

(56) References Cited

U.S. PATENT DOCUMENTS

| | | | | |
|---|---|---|---|---|
| 7,250,553 | B2 * | 7/2007 | Liu ................... | C12N 15/8241 800/270 |
| 2014/0154397 | A1 * | 6/2014 | Rommens ............ | C12N 15/825 426/637 |

OTHER PUBLICATIONS

Ipsaro et al. Rapid generation of drug-resistance alleles at endogenous loci using CRISPR-Cas9 indel mutagenesis. PloS One. Feb. 23, 2017;12(2):e0172177. eCollection 2017. (Year: 2017).*
Seruggia et al. Functional validation of mouse tyrosinase non-coding regulatory DNA elements by CRISPR-Cas9-mediated mutagenesis. Nucleic Acids Res. May 26, 2015;43(10):4855-67. Epub Apr. 20, 2015. (Year: 2015).*
Shan et al. Targeted genome modification of crop plants using a CRISPR-Cas system. Nat Biotechnol 31, 686-688 (2013). (Year: 2013).*
Mohr et al. CRISPR guide RNA design for research applications. FEBS J. Sep. 2016;283(17):3232-8. Epub Jun. 22, 2016. (Year: 2016).*
B. Farboud et al: "Dramatic Enhancement of Genome Editing by CRISPR/Cas9 Through Improved Guide RNA Design", Genetics, vol. 199, No. 4, Feb. 18, 2015 (Feb. 18, 2015), pp. 959-971, XP055284263, US ISSN: 0016-6731, DOI: 10.1534/genetics.115. 175166 (the whole document).
International Search Report mailed Sep. 9, 2018 received in corresponding International Application No. PCT/EP2018/074150.
Ipsaro Jonathan J et al: "Rapid 1-11,14,generation of drug-resistance alleles at endogenous loci using CRISPR-Cas9 indel mutagenesis", Plos One,vol. 12, No. 2, E172177, Feb. 23, 2017 (Feb. 23. 2017), pp. 1-16,XP002776886, ISSN: 1932-6203, DOI: 10.1371/journal.pone.0172177 p. 2, paragraph 2, p. 7, line 10, paragraph 1—p. 13. paragraph 1; figures 1-3.
Qiwei Shan, et al.: "Targeted genome modification of crop plants using a CRISPR-Cas system", Nature Biotechnology (Advance Online Publication), vol. 31, No. 8, Aug. 1, 2013 (Aug. 1, 2013), pp. 686-688, XP055216828, ISSN: 1087-0156, DOI: 10.1038/nbt.2650 (the whole document).
Seruggia Davide et al: "Functional validation of mouse tyrosinase non-coding regulatory DNA elements byCRISPR-Cas9-mediated mutagenesis", Nucleic Acids Research, vol. 43, No. 10, May 26, 2015 (May 26, 2015), pp. 4855-4867, XP002776888, ISSN: 0305-1048 (the whole document).
Wiel C C Van De et al: "New traits in crops produced by genome editing techniques based on deletions", Plant Biotechnology Reports, vol. 11, No. 1,Feb. 13, 2017 (Feb. 13. 2017), pp. 1-8, XP036195063, Springer Japan, JP, ISSN: 1863-5466, DOI:10.1007/S11816-017-0425-Z [retrieved on Feb. 13. 2017] (the whole document).
Yoder Kristine E et al: "Host Double Strand Break Repair Generates HIV-1 Strains Resistant to CRISPR/Cas9", Scientific Reports, vol. 6, 29530, Jul. 12, 2016 (Jul. 12, 2016), pp. 1-12, XP002776887, ISSN: 2045-2322, DOI: 10.1038/srep 29530 p. 3, last paragraph—p. 5, last paragraph; examples 2-6.

* cited by examiner

*Primary Examiner* — Cynthia E Collins
(74) *Attorney, Agent, or Firm* — Troutman Pepper Hamilton Sanders LLP

(57) ABSTRACT

The invention pertains to the targeted alteration of a duplex DNA in a cell, whereby two site-specific nucleases generate an indel, such that the open reading frame is not altered after the second indel. The invention further pertains to the use of such nucleases for the targeted alteration of an open reading frame in duplex DNA and a kit of parts for use in a method of the invention. Using the method of the invention, novel plants were obtained having an improved herbicide resistance. The invention therefore also concerns plants having improved herbicide resistance due to the expression of an altered ALS protein.

Figure 1A:
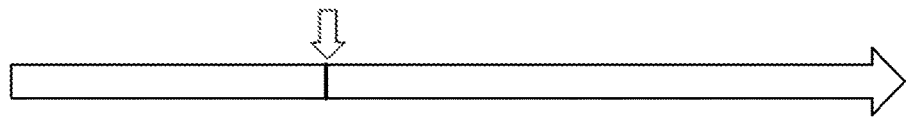

12 Claims, 6 Drawing Sheets
Specification includes a Sequence Listing.

Fig. 2

KG10177

GGAGTGATCAAAAGTCCCACATCGATCAGGTGATATATAGCAGCTTAGTTTATATAATGATAGAGTCGACATAGCGATTG
CAAGTGCCGAGGAGGATGATGTTTTAGAGCTAGAAATAGCAAGTTAAAATAAGGCTAGTCCGTTATCAACTTGAAAAAGTGGCACC
GAGTCGGTGCTTTTTTTCTAGACCCAGCTTTCTTGTACAAAGTTGGCATTACGCT

KG10190

GGAGTGATCAAAAGTCCCACATCGATCAGGTGATATATAGCAGCTTAGTTTATATAATGATAGAGTCGACATAGCGATTG
CATCCTCCTCGGCACTTGACGTTTTAGAGCTAGAAATAGCAAGTTAAAATAAGGCTAGTCCGTTATCAACTTGAAAAAGTGGCACC
GAGTCGGTGCTTTTTTTCTAGACCCAGCTTTCTTGTACAAAGTTGGCATTACGCT

KG10191

GGAGTGATCAAAAGTCCCACATCGATCAGGTGATATATAGCAGCTTAGTTTATATAATGATAGAGTCGACATAGCGATTG
TTACCGGTCAAGTGCCGAGGGTTTTAGAGCTAGAAATAGCAAGTTAAAATAAGGCTAGTCCGTTATCAACTTGAAAAAGTGGCACC
GAGTCGGTGCTTTTTTTCTAGACCCAGCTTTCTTGTACAAAGTTGGCATTACGCT

KG10240

GGAGTGATCAAAAGTCCCACATCGATCAGGTGATATATAGCAGCTTAGTTTATATAATGATAGAGTCGACATAGCGATTG
AACAAAGCACCAGTGGTCTAGTGGTAGAATAGTACCCTGCCACGGTACAGACCCGGGTTCGATTCCCGGCTGGTGCA
CAAGTGCCGAGGAGGATGATGTTTTAGAGCTAGAAATAGCAAGTTAAAATAAGGCTAGTCCGTTATCAACTTGAAAAAGTGGCACC
GAGTCGGTGC

AACAAAGCACCAGTGGTCTAGTGGTAGAATAGTACCCTGCCACGGTACAGACCCGGGTTCGATTCCCGGCTGGTGCA

CATCCTCCTCGGCACTTGACGTTTTAGAGCTAGAAATAGCAAGTTAAAATAAGGCTAGTCCGTTATCAACTTGAAAAAGTGGCACC
GAGTCGGTGC

AACAAAGCACCAGTGGTCTAGTGGTAGAATAGTACCCTGCCACGGTACAGACCCGGGTTCGATTCCCGGCTGGTGCA

TTACCGGTCAAGTGCCGAGGGTTTTAGAGCTAGAAATAGCAAGTTAAAATAAGGCTAGTCCGTTATCAACTTGAAAAAGTGGCACC
GAGTCGGTGCTTTTTTTCTAGACCCAGCTTTCTTGTACAAAGTTGGCATTACGCT

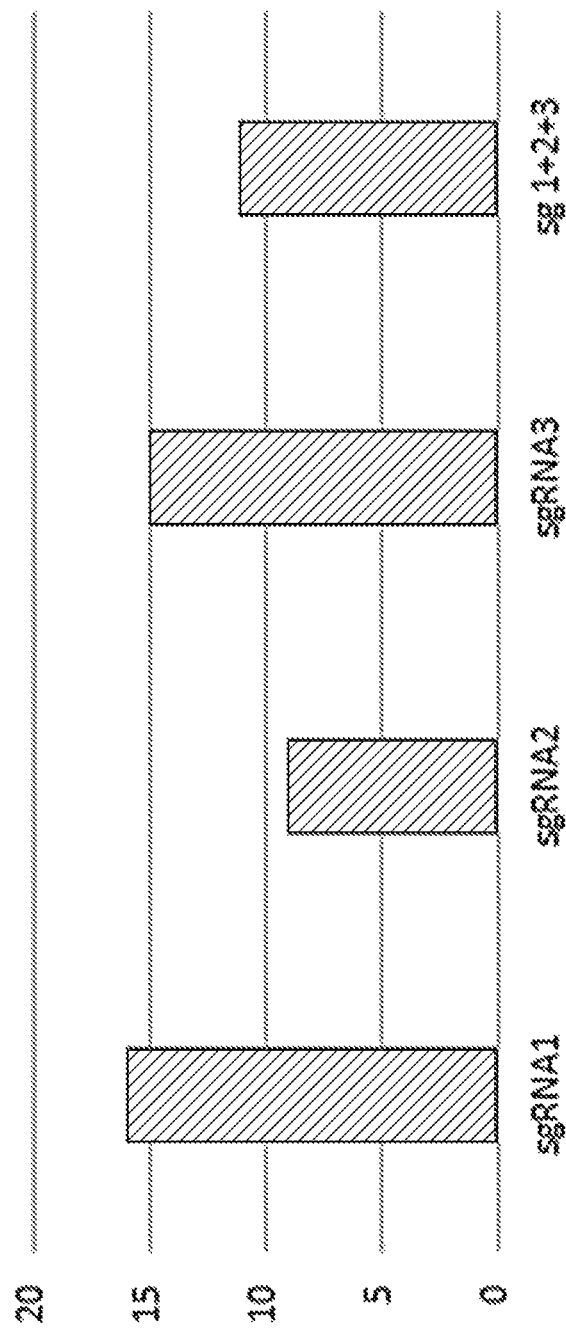

Fig. 3B

| | | |
|---|---|---|
| ALS2 | ATTA<u>CCG</u>GTCAAGTGCCGAGG<u>AGG</u>ATGAT<u>TGG</u> | |
| sgRNA1 | ATTACCGGTCAAGTGCCGAGGAGGATTGATTGG | 5.8% |
| | ATTACCGGTCAAGTGCCG----GGATGATTGG | 2.1% |
| | ATTACCGGTCAAGTGCCGA---GGATGATTGG | 1.5% |
| | ATTACCGGTCAAGTGCCGAGGAG----ATTGG | 0.7% |
| sgRNA2 | ATTACCGGTCAAAGTGCCGAGGAGGATGATTGG | 4.3% |
| | ATTACCGGTCA-GTGCCGAGGAGGATGATTGG | 1% |
| | ATTACCGGTC--GTGCCGAGGAGGATGATTGG | 1% |
| | ATTACCGGTCA--TGCCGAGGAGGATGATTGG | 0.4% |
| sgRNA3 | ATTACCGGTCAAGTGCC-AGGAGGATGATTGG | 8.7% |
| | ATTACCGGTCAAG-------GAGGATGATTGG | 0.5% |
| | ATTACCGGTCAAGTGCCGCAGGAGGATGATTGG | 0.5% |
| | ATTACCGGTCAAGTGCCGTAGGAGGATGATTGG | 0.5% |
| sg1+2+3 | ATTACCGGTCAAGTGCCG----GGATGATTGG | 1.1% |
| | ATTACCGGTCAAGTGCC-AGGAGGATGATTGG | 1.1% |
| | ATTACCGGTCAAGTGCCGAG-------ATTGG | 0.8% |
| | ATTACCGGTC----GCCGAGGAGGATTGATTGG | 0.6% |
| | ATTACCGGTCAAGTGCCGTAGGAGG--GATTGG | 0.6% |
| | ATTACCGGTCAAGTGCC-AGGAGGA-GATTGG | 0.5% |
| | ATTACCGGTC---TGCCGAGGAGGATTGATTGG | 0.5% |
| | ATTACCGGTCA----GCCGAGGAGGAT---TGG | 0.3% |

Fig. 3C

```
ALS1      ATTACAGGTCAAGTGCCAAGGAGGATGATTGG
sgRNA1    ATTACAGGTCAAGTGCCAAGGAGGAT-ATTGG      4.3%
          ATTACAGGTCAAGTGCCAAGGAGGATTGATTGG     1.7%
          ATTACAGGTCAAGTGCCAAGGAGG---ATTGG      1.1%
          ATTACAGGTCAAGTGCCAAGGAGG-GATTGG       0.8%
sgRNA3    ATTACAGGTCAAGTGCCAAAGGAGGATGATTGG     0.7%
          ATTACAGGTCAAG-------GAGGATGATTGG      0.4%
          ATTACAGGTCAAGTGCCA-GGAGGATGATTGG      0.3%
          ATTACAGGTCAAGT----AGGAGGATGATTGG      0.2%
Sg1+2+3   ATTACAGGTCAAGTGCCA-GGAGGATGATTGG      5.7%
          ATTACAGGTCAAGTGCCAA---GGATGATTGG      3.9%
          ATTACAGGTCAAGTGCCAAGGAG----ATTGG      2.8%
          ATTACAGGTCAAGTGCCAAGGAGGATTGATTGG     2.6%
          ATTACAGGTCAAGTGCCAAAGGAGGATTGATTGG    2.1%
          ATTACAGGTCAAGTGCCA-GGAGGATTGATTGG     1.8%
          ATTACAGGTCAAGTGCCA-GGAGG--GATTGG      0.5%
          ATTACAGGTCAAGT----AGGAGGATTGATTGG     0.5%
```

Fig. 4A

```
ALS1      GCTATTACAGGTCAAGTGCCAAGGAGGATGATTGGTACT
           A  I  T  G  Q  V  P  R  R  M  I  G  T
ALS2      GCTATTACCGGTCAAGTGCCGAGGAGGATGATTGGTACT sgRNA1(+)         ------------------------
sgRNA2(-)              ------------------------
sgRNA3(+)  ------------------------
```

Fig. 4B

| | | | |
|---|---|---|---|
| WT ALS2 | GGTCAAGTGCCGAGGAGGATGATT | GQVPRRMIGT | |
| C22 ALS2 | GGTCA-GTGCCGAGGAGGATTGATT | GQCRGGLIGT | 2+1 |
| C34 ALS2 | GGTCA-GTGCCGAGGAGGATTGATT | GQCRGGLIGT | 2+1 |
| C17 ALS2 | GGTCAAAGTGCC-AGGAGGATGATT | GQSARRMIGT | 2+3 |
| C37 ALS2 | GGTCAAAGTGCC-AGGAGGATGATT | GQSARRMIGT | 2+3 |
| C24 ALS2 | GGTCA-GTGCCGAGGAGGATTGATT | GQCRGGLIGT | 2+1 |
| C27 ALS2 | GGTCA-GTGCCGAGGAGGATTGATT | GQCRGGLIGT | 2+1 |
| C33 ALS2 | GGTCA-GTGCCGAGGAGGATTGATT | GQCRGGLIGT | 2+1 |
| C35 ALS2 | GGTCAAAGTGCC-AGGAGGATGATT | GQSARRMIGT | 2+3 |
| | | | |
| WT ALS1 | GGTCAAGTGCCAAGGAGGATGATT | GQVPRRMIGT | |
| C14 ALS1 | GGTCAAGTGC-AAGGAGGATTGATT | GQVQGGLIGT | 3+1 |

BALANCED INDELS

CROSS REFERENCE TO RELATED APPLICATIONS

This application is a continuation of International Patent Application No. PCT/EP2018/074150, filed Sep. 7, 2018, published on Mar. 14, 2019 as WO 2019/048618 A1, which claims priority to European Patent Application No. 17190057.4, filed Sep. 8, 2017. The contents of these applications are herein incorporated by reference in their entirety.

SEQUENCE LISTING

The instant application contains a Sequence Listing which is being submitted in ASCII format via EFS-WEB and is hereby incorporated by reference in its entirety. Said ASCII copy, created on Nov. 16, 2020, is named 085342-3500_SL.txt and is 79,552 bytes.

FIELD OF THE INVENTION

The present invention concerns the targeted mutagenesis and modifications of duplex DNA in a cell, including methods and compositions for making such mutations and modifications.

BACKGROUND

The process of deliberately creating changes in the genetic material of living cells has the goal of modifying one or more genetically encoded biological properties of that cell, or of the organism of which the cell forms part or into which it can regenerate. These changes can e.g. take the form of deletion of parts of the genetic material, addition of exogenous genetic material, or changes in the existing nucleotide sequence of the genetic material. Methods of altering the genetic material of eukaryotic organisms have been known for over 20 years, and have found widespread application in plant, human and animal cells and microorganisms for improvements in the fields of agriculture, human health, food quality and environmental protection. The most common methods consist of adding exogenous DNA fragments to the genome of a cell, which will then confer a new property to that cell or its organism over and above the properties encoded by already existing genes, including applications in which the expression of existing genes will thereby be suppressed. Although many such examples are effective in obtaining the desired properties, these methods have several drawbacks. For example, these conventional methods are not very precise, because there is not always control over the genomic positions in which the exogenous DNA fragments are inserted (and hence over the ultimate levels of expression), and the desired effect will have to manifest itself over the natural properties encoded by the original and well-balanced genome. On the contrary, methods of genome editing that will result in the addition, deletion or conversion of nucleotides in predefined genomic loci will allow the precise modification of existing genes.

Recently a novel method for genome editing has been reported. CRISPRs (Clustered Regularly Interspaced Short Palindromic Repeats) are loci containing multiple short direct repeats and are found in 40% of the sequenced bacteria and 90% of sequenced archaea. The CRISPR repeats form a system of acquired bacterial immunity against genetic pathogens such as bacteriophages and plasmids. When a bacterium is challenged with a pathogen, a small piece of the pathogen's genome is processed by CRISPR associated proteins (Cas) and incorporated into the bacterial genome between CRISPR repeats. The CRISPR loci are then transcribed and processed to form so called crRNAs which include approximately 30 bps of sequence identical to the pathogen's genome. These RNA molecules form the basis for the recognition of the pathogen upon a subsequent infection and lead to silencing of the pathogen genetic elements through direct digestion of the pathogen's genome. The Cas9 protein is an essential component of the type-II CRISPR/Cas system from S. pyogenes and forms an endonuclease, when combined with the crRNA and a second RNA termed the trans-activating crRNA (tracrRNA), which targets the invading pathogenic DNA for degradation by the introduction of DNA double strand breaks (DSBs) at the position in the genome defined by the crRNA. Recently, Jinek et al. (2012, Science 337: 816-820) demonstrated that a single chain chimeric RNA (single guide RNA, sRNA, sgRNA), produced by combining the essential sequences of the crRNA and tracrRNA into a single RNA molecule, was able to form a functional endonuclease in combination with Cas9. Many different CRISPR/Cas systems have been identified from different bacterial species (Zetsche et al. 2015 Cell 163, 759-771; Kim et al. 2017, Nat. Commun. 8, 1-7; Ran et al. 2015. Nature 520, 186-191).

The CRISPR/Cas9 system can be used for genome editing in a wide range of different organisms and cell types. First a genomic sequence is identified at which the CRISPR/Cas endonuclease should induce a DSB and this is then screened for the presence of a protospacer adjacent motif (PAM). The PAM sequence is essential for the CRISPR/Cas endonuclease activity, is relatively short, and is therefore usually present multiple times in any given sequence of some length. For instance the PAM motif of the S. pyogenes Cas9 protein is NGG, which ensures that for any given genomic sequence multiple PAM motifs are present and so many different guide RNAs can be designed. In addition, guide RNAs can also be designed targeting the opposite strands of the same double strand sequence. The sequence immediately adjacent to the PAM is incorporated into the guide RNA. This can differ in length depending upon the CRISPR/Cas system being used. For instance, the optimal length for the targeting sequence in the Cas9 sgRNA is 20 nt, and in most cases a sequence of this length is unique in a plant genome. For expression in plant cells a gene coding for a guide RNA can be linked to an RNA polymerase-III promoter, such as the U6 promoter from *Arabidopsis*, or the corresponding or functionally similar pol-III promoter from the cell type, organism, plant species or family in which the experiments are being performed.

The CRISPR/Cas endonuclease can be expressed in the cell from any form of constitutive or inducible promoter that is suitable for the organism or cell type in which the experiments are being performed. In some instances, the protein expression levels of the CRISPR/Cas endonuclease can be improved by optimization of its codon usage for the specific cell type or organism.

The two components of the CRISPR/Cas system, the endonuclease and the targeting RNA(s) can be expressed in the cell from ectopic genomic elements such as (non-replicating) plasmid constructs, viral vectors or introduced directly in the cells or organism as protein (the CRISPR/Cas endonuclease) and RNA (guide RNA). In addition mRNA encoding the CRISPR/Cas endonuclease can be used. When the plasmid or viral vectors are unable to replicate in the transformed cells then the CRISPR/Cas and guide RNA(s)

are expressed or present for a short period and then are eliminated from the cell. Stable expression of the CRISPR/Cas protein and guide RNA can be achieved using a transgenic approach whereby the genes coding for them are integrated into the host genome.

Once the CRISPR/Cas endonuclease and the guide RNA is present/expressed in the cell then the complex of the two components scans the genomic DNA for the sequence complementary to the targeting sequence on the guide RNA and adjacent to a PAM sequence. Depending on the CRISPR/Cas endonuclease being used, the complex then induces nicks in both of the DNA strands at varying distances from the PAM. For instance the *S. pyogenes* Cas9 protein introduces nicks in the both DNA strands 3 bps upstream from the PAM sequence to create a blunt DNA DSB. Once a DNA DSB has been produced the cellular DNA repair machinery, particularly proteins belonging to the non-homologous end joining (NHEJ) pathway, are involved in the re-ligation of the DNA ends. If this DSB is repaired accurately then the sequence again forms a target for cutting by the CRISPR/Cas-guide RNA complex. However, some re-ligation events are imprecise and can lead to the random loss or gain of a few nucleotides at the break, resulting in an indel mutation in the genomic DNA. This results in an alteration of the target sequence that prevents binding of the guide RNA and thus any further DSB induction. When a DSB is induced in a coding sequence, indels may be produced that lead to an alteration in the protein reading frame and will generate a null mutation. Alternatively, any indels which lead to the deletion or insertion of multiples of three nucleotides (e.g. +3, +9, −6) will create in frame mutations which may only influence protein function rather than eliminating it. Ipsaro et al (PLoS One. 2017; 12(2):e0172177) teaches the introduction of a single guide RNA, wherein the double-stranded break produced such rare in-frame mutation, affecting a few amino acid residues. Nevertheless, the chance that the introduction of a single guide RNA results in an in-frame mutation is extremely low.

Recently there have been several publications that describe the creation of indel mutations in plant cells using the CRISPR/Cas9 system (Li et al. (2013) Nat. Biotech. 31:688-691; Shan et al. (2013) Nat. Biotech. 31:686-688; Nekrasov et al. (2013) Nat. Biotech. 31:691-693; Feng et al. (2013) Cell Res. 23:1229-1231). In all of these studies the production of the Cas9 protein and the chimeric RNA in the plant cell is achieved using DNA-based expression vectors such as plasmids or T-DNA. These were introduced into plant protoplasts or integrated into the plant genome and then cells or regenerated plants containing INDEL mutations at the target sequences were identified. Other publications have described the introduction of the Cas9 protein and in vitro expressed guide RNA into plant protoplasts to create mutations (Malnoy et al. (2016) Front. Plant Sci. 7: 1904) and also the regeneration of these protoplasts into plants (Woo et al. (2015) Nat. Biotech. 33 (11): 1162-1165).

It has further been described in the art that two single guide RNAs can be introduced in the same cell, wherein each gRNA targets a different CDS aiming for editing two separate loci (Farboud and Meyer, Genetics, 2015 April; 199(4):959-71). Further, two single guide RNAs have been introduced in a single cell for producing DSBs at separate non-coding regions in the same DNA molecule with the aim to delete or inverse the intervening a non-coding regulatory DNA element (Seruggia et al, 2015, Nucleic Acids Res.; 43(10):4855-67).

The creation of null alleles is a very powerful technique to study gene function and allows to investigate the effect of the loss of a gene on the phenotype of the cell or organism. The production of null alleles can give very extreme phenotypes and often in plant breeding more subtle forms of allelic variation can be more valuable. For instance, changes in single amino acids have the potential to create superior alleles with commercially interesting phenotypes. Therefore, techniques that are able to alter individual (or adjacent) nucleotides are also valuable. Recently, a variation of the CRISPR/Cas system was published (Komor et al. 2016. Nature 533, 420-424; Zong et al. 2017. Nat. Biotech. 35, 438-440; Shimitani et al. 2017. Nat. Biotech. 35,441-443) that consists of a fusion of a CRISPR/Cas endonuclease to a cytosine deaminase protein. In this case the fusion protein is targeted to a specific genomic sequence where specific cytosines are converted to thymines, altering the codons in a coding sequence to change individual amino acids within a protein, whereby the reading frame of the gene is not changed. However, altering single amino acids may often be insufficient to alter the protein function. In addition, not all C to T changes will alter the encoded amino acid. There is thus still a need in the art for an efficient method to alter pre-determined amino acid stretches.

Allelic variation could be increased to a level in between the benign effects of single point mutations and the severe effects of null alleles, e.g. whereby several (pre-determined) adjacent amino acids are altered simultaneously. There is therefore a need for the development of techniques that make this possible, for example for, but not limited to, use in developing new mutants that result in resistance to one or more herbicides such as ALS mutants.

The acetolactate synthase gene (ALS) found in plants and bacteria is an essential protein involved in the synthesis of branched amino acids (valine, leucine and isoleucine). ALS is also the target protein of several known herbicides such as sulfonylureas (SU), imidazolinones (IM), triazalopyrimidines (TP), pyrimidinyl oxybenzoates (POBs) and sulfonylamino carbonyl triazolinones (SCTs). There are a number of dominant ALS mutations known that confer varying degrees of herbicide tolerance to one or several classes of the ALS inhibitors (Roux et al. 2005. Weed Res. 45, 220-227). Many of the mutations that confer resistance to the SU class of herbicides are in or around the codon for P184 (e.g. P184L, P184R, P184Q etc). Such mutations arise spontaneously in weed species or have been selected for in crop species during tissue culture propagation or random mutagenesis approaches. The usefulness of such mutations is variable, depending upon the herbicide/crop combination and the level of resistance that the mutation is able to confer on the plant. There are a number of SU class herbicides, such as amidosulfuron, azimsulfuron, bensulfuron-methyl, chlorsulfuron, cinosulfuron, flazasulfuron, flupyrsulfuron-methyl, foramsulfuron, Iodosulfuron, mesosulfuron, metsulfuron-methyl, nicosulfuron, rimsulfuron, sulfosulfuron, thifensulfuron-methyl, triasulfuron, tribenuron-methyl, triflusulfuron-methyl, imazamox, imazapyr, imazaquin and metosulam, many of which are used in commercial formulations. Therefore, there is also a need to identify novel ALS resistance mutations that confer a resistance to (1) broader range of compounds and/or (2) an increased concentration of herbicide.

Using the method of the invention, we have identified new herbicide resistance ALS alleles that could be engineered in other crop species.

Hence the mutagenesis of DNA (e.g. as a result of exposure to mutagens) to screen for new properties is long known in the art. Such mutations are however often created at a random location in one or more protein coding sequences. Alternatively protein-encoding DNA can be mutated, e.g. cleaved, at specific locations. The mutated DNA may consequently comprise one or more indels at the previously cleaved location, thereby causing a frame shift after the cleaved location. Such frame shift usually leads to a loss of function of the protein.

Such drastic loss of function is however not always preferred, e.g. especially if the mutated protein fulfils a function of interest. In such cases, it may instead be desired to modify short predetermined stretches of the protein, e.g. in order to alter its function. There is therefore still a strong need in the art to selectively modify only specific parts of a protein. In particular, there is a need in the art to randomly alter specific parts of a protein coding sequence in a straight-forward manner to generate mutated proteins, for example to screen for new properties conferred by the mutated protein.

SUMMARY

In a first aspect, the invention relates to a method for targeted alteration of a coding sequence (CDS) in duplex DNA, wherein the method comprises a step of exposing the duplex DNA to at least two site-specific nucleases, wherein a first site-specific nuclease cleaves the DNA generating a first indel at a first location within the ORF and wherein a second site-specific nuclease cleaves the DNA generating a second indel at a second location within the same CDS, wherein the CDS before the first indel and after the second indel remain in the same reading frame, and wherein the altered CDS does not comprise a stop codon.

Preferably, the CDS is altered by introducing or deleting at least one nucleotide at the first location and by introducing or deleting at least one nucleotide at the second location, wherein the total of introduced nucleotides preferably is 0, 3, 6, 9 or 12 and/or wherein the total of deleted nucleotides preferably is 0, 3, 6, 9 or 12.

In a preferred method, the length of the altered CDS is between about 1-300 codons, preferably between about 1-250, 1-200, 1-150, 1-100, 1-50, 1-25, 1-20, 1-15, 1-10 or 1-5 codons.

Preferably, at least one of the nucleases is a CRISPR nuclease and wherein the method further comprises exposing the duplex DNA to:
i) a first guide RNA that comprises a first guide sequence for targeting the first nuclease to the first location in the duplex DNA; and/or
ii) a second guide RNA that comprises a second guide sequence for targeting the second nuclease to the second location in the duplex DNA.

Preferably, the at least one CRISPR nuclease is Cas9 or Cpf1.

In a preferred embodiment, at least one of the nucleases is selected from the group consisting of a zinc finger nuclease, a meganuclease and a TALEN.

Preferably, the duplex DNA is exposed to two, three or four site-specific nucleases and wherein the two, three or four site-specific nucleases cleave the duplex DNA of the same CDS.

In a preferred method of the invention, wherein the duplex DNA is in a cell.

Preferably, the cell is transformed with at least one of the site-specific nucleases and/or at least one of the guide RNAs.

Preferably, the cell is transfected with a nucleic acid construct encoding at least one of the site specific nucleases and/or at least one of the guide RNAs, wherein the nucleic acid construct preferably encodes at least two guide RNAs.

Preferably, the method of the invention further comprises the step of regenerating a plant or descendent thereof comprising the targeted alteration.

In a second aspect, the invention pertains to a plant obtainable by the method as defined herein, wherein the plant is modified by comprising a targeted alteration when compared to a control, and wherein the control is a plant before the targeted alteration was introduced, wherein the plant preferably comprises at least one altered ALS gene having
i) at least 80% sequence identity with SEQ ID No. 1 and wherein position 547-570 has at least 85% sequence identity with any one of SEQ ID No. 3-5; or
ii) wherein the ALS gene has at least 80% sequence identity with SEQ ID No. 2 and wherein position 541-564 has at least 85% sequence identity with any one of SEQ ID No. 3-5;
and wherein the plant has an improved herbicide resistance as compared to the control.

In a third aspect, the invention relates to a plant having an improved herbicide resistance, wherein the plant has been genetically engineered to express at least one altered ALS protein that comprises an amino acid sequence having
i) at least 80% sequence identity with SEQ ID No. 9 and wherein positions 183-192 has at least 85% sequence identity with any one of SEQ ID NO. 11-13; or
ii) at least 80% sequence identity with SEQ ID No. 10 and wherein positions 181-190 has at least 85% sequence identity with any one of SEQ ID NO. 11-13; and
wherein the plant has an improved herbicide resistance compared to the same plant that does not express the altered ALS protein.

In a fourth aspect, the invention concerns a kit of parts for use in a method of the invention, comprising:
a container comprising a site-specific nuclease and/or a nucleic acid construct encoding the site-specific nuclease;
a manual for targeted alteration of an CDS in duplex DNA in a cell according to the method of the invention; and optionally
a second container comprising at least two guide RNAs or at least one nucleic acid construct encoding at least one guide RNA,
wherein the first container preferably comprises
i) at least two site-specific nucleases;
ii) at least two nucleic acid constructs encoding the site-specific nucleases; or
iii) a nucleic acid construct encoding at least two site-specific nucleases.

In a fifth aspect, the invention pertain to the use of at least two site-specific nucleases as defined herein or a kit of part as defined herein for the targeted alteration of an CDS in duplex DNA in a cell.

Definitions

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

"A," "an," and "the": these singular form terms include plural referents unless the content clearly dictates otherwise. The indefinite article "a" or "an" thus usually means "at least one". Thus, for example, reference to "a cell" includes a combination of two or more cells, and the like.

"About" and "approximately": these terms, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods. Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

"And/or": The term "and/or" refers to a situation wherein one or more of the stated cases may occur, alone or in combination with at least one of the stated cases, up to with all of the stated cases.

"Comprising": this term is construed as being inclusive and open ended, and not exclusive. Specifically, the term and variations thereof mean the specified features, steps or components are included. These terms are not to be interpreted to exclude the presence of other features, steps or components.

Exemplary": this terms means "serving as an example, instance, or illustration," and should not be construed as excluding other configurations disclosed herein.

"Plant": this includes plant cells, plant protoplasts, plant cell tissue cultures from which plants can be regenerated, plant calli, plant clumps, and plant cells that are intact in plants or parts of plants such as embryos, pollen, ovules, gametes, seeds, leaves, flowers, branches, fruit, kernels, ears, cobs, husks, stalks, roots, root tips, anthers, grains and the like. "Plant cell(s)" include protoplasts, gametes, suspension cultures, microspores, pollen grains, etc., either in isolation or within a tissue, organ or organism.

Construct" or "nucleic acid construct" or "vector": this refers to a man-made nucleic acid molecule resulting from the use of recombinant DNA technology and which is used to deliver exogenous DNA into a host cell, often with the purpose of expression in the host cell of a DNA region comprised on the construct. The vector backbone of a construct may for example be a plasmid into which a (chimeric) gene is integrated or, if a suitable transcription regulatory sequence is already present (for example a (inducible) promoter), only a desired nucleotide sequence (e.g. a coding sequence) is integrated downstream of the transcription regulatory sequence. Vectors may comprise further genetic elements to facilitate their use in molecular cloning, such as e.g. selectable markers, multiple cloning sites and the like.

"Sequence" or "Nucleotide sequence": This refers to the order of nucleotides of, or within a nucleic acid. In other words, any order of nucleotides in a nucleic acid may be referred to as a sequence or nucleotide sequence.

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide.

The term "complementarity" is herein defined as the sequence identity of a sequence to a fully complementary strand (defined herein below, e.g. the second strand). For example, a sequence that is 100% complementary (or fully complementary) is herein understood as having 100% sequence identity with the complementary strand and e.g. a sequence that is 80% complementary is herein understood as having 80% sequence identity to the (fully) complementary strand.

"Identity" and "similarity" can be readily calculated by known methods. "Sequence identity" and "sequence similarity" can be determined by alignment of two peptide or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blosum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at http://www.ncbi.nlm.nih.gov/.

A "target sequence" is to denote an order of nucleotides within a nucleic acid that is to be targeted, e.g. wherein an alteration is to be introduced or to be detected. For example, the target sequence is an order of nucleotides comprised by a first strand of a DNA duplex.

An "endonuclease" is an enzyme that hydrolyses at least one strand of a duplex DNA upon binding to its recognition site. An endonuclease is to be understood herein as a site-specific endonuclease and the terms "endonuclease" and "nuclease" are used interchangeable herein. A restriction endonuclease is to be understood herein as an cndonucicasc that hydrolyses both strands of the duplex at the same time to introduce a double strand break in the DNA. A "nicking" endonuclease is an endonuclease that hydrolyses only one strand of the duplex to produce DNA molecules that are "nicked" rather than cleaved.

DETAILED DESCRIPTION OF THE INVENTION

Figure 1B:
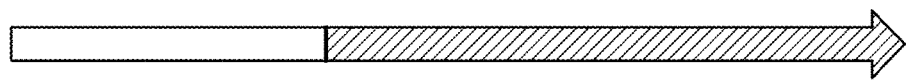
Figure 1C:
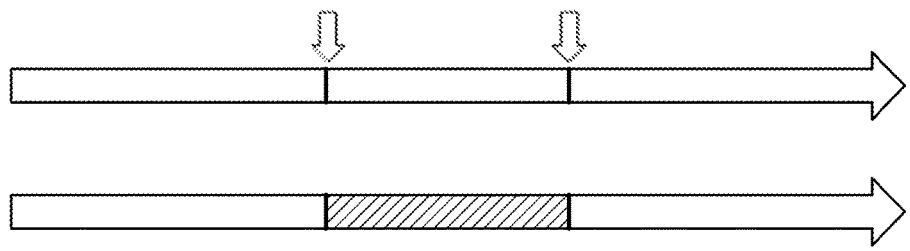

The generation of a double-stranded break within a coding sequence (CDS) by a single site-specific nuclease is used to create a frame shift caused by an indel at the position of the double-stranded break, predominantly resulting in a dis-functional protein. The inventors have now discovered a novel and effective method for generating mutants wherein only a predetermined, e.g. small, part of the CDS is altered and the reading frame is maintained, by exposing duplex DNA to two site-specific endonucleases. The inventors came to the insight that generating two double-stranded breaks within a single CDS may result in an altered CDS only in between the two locations where indels are generated (FIGS. 1A-1C).

The term "altered CDS" is therefore defined herein as the CDS starting with the first indel up to and including the second indel. The altered CDS may lead to altered properties of the protein, e.g. increasing or decreasing its functionality. Put differently, instead of a complete loss of protein functionality, the generation of double-stranded breaks can be used to e.g. subtly alter the functionality of a protein.

Therefore in a first aspect, the invention pertains to a method for targeted alteration of a CDS in duplex DNA, wherein the method comprises a step of exposing the duplex DNA to at least two site-specific nucleases, wherein a first site-specific nuclease cleaves the DNA generating a first indel at a first location within the CDS, wherein a second site-specific nuclease cleaves the DNA generating a second indel at a second location within the same CDS, and wherein the CDS before the first indel and after the second indel remains in the same reading frame.

The invention further pertains to a method for producing a duplex DNA molecule comprising an altered CDS, wherein the altered CDS is produced by a targeted alteration as defined herein.

Preferably the altered CDS does not comprise a stop codon. The first and second location may be within the same exon of the CDS. However, it is also feasible that the first location is in an exon upstream (i.e. 5' as regarded from the coding strand perspective) of the exon comprising the second location. Hence in an embodiment, the exon comprising the first location and the exon comprising the second location can be separated by at least one intron, e.g. can be separated by 1, 2, 3, 4, 5, 6, 7, 8, 9, 10 or more introns.

Preferably, the first and second location within the CDS are outside the 5'-terminal start codon, the 3'-terminal stop codon and any functional splice site that is part of the CDS and that is required for removal of introns from precursor messenger RNA to form mature mRNA during splicing. In other words, preferably the method of the invention renders the 5'-terminal start codon, the 3'-terminal stop codon and/or any functional splice site within the CDS intact.

The targeted alteration of the method of the invention may be performed outside of a cell, wherein the DNA is in a matrix that allows for the site-specific nucleases to introduce a double strand break, and that comprises enzymes that allows for NHEJ. The DNA comprising the targeted alteration may be introduced into the cell for subsequent translation of the protein. Alternatively, protein translation may also occur outside of a cell. Preferably, targeted alteration of the method of the invention is in a cell or intracellular, more preferably in a cell as further detailed herein.

The method of the invention is preferably used to e.g. screen for mutated proteins having an altered functionality in comparison to the non-mutated protein by altering only a specific part of the CDS. For example, the functionality of the mutated protein may be increased or decreased as compared to the functionality of the non-mutated protein. It is further contemplated within the invention that the mutated proteins may have a de novo functionality, e.g. a functionality not previously present in the non-mutated protein, such as a novel interaction with a (novel) substrate. In addition, the method of the invention can be used to e.g. inactivate the active domain of an enzyme, or to alter the specificity of binding domains e.g. for a receptor-ligand interaction, without altering the remainder of the protein. Hence, the method of the invention allows for a tool to specifically alter a part of a CDS and the skilled person understands that such method will find wide application. Targeted alteration of the CDS is to be understood herein as an alteration of a CDS at (at least one) specific, e.g. predetermined location. Said alteration is preferably a frame shift, preferably through the introduction or deletion of at least one nucleotide.

Said specific location within the CDS is preferably determined by a target sequence, preferably a stretch of contiguous nucleotides that is present in the first strand of the DNA duplex. The duplex DNA in a cell comprises a first DNA strand a second DNA strand. The second DNA strand is the complement of the first DNA strand and pairs to it to form the duplex. For example, a complement of a first DNA strand sequence ATTT (in the 5' to 3' direction) is TAAA (in the 3' to 5' direction). The DNA of the duplex DNA may be any type of DNA, endogenous or exogenous to the cell, for example genomic DNA, chromosomal DNA, artificial chromosomes, plasmid DNA, or episomal DNA. The duplex may be nuclear or organellar (e.g. mitochondrial) DNA. Preferably the DNA duplex is chromosomal DNA, preferably endogenous to the cell. It further is to be understood herein that the target sequence may be a transgene or an endogenous gene of the cell.

Within the context of the current invention, the first DNA strand of the DNA duplex comprises a CDS and the second strand comprises a second nucleic acid sequence that is complementary to the CDS. A coding sequence or CDS is defined as the portion of the DNA that is composed of one or more subsequent exons that together code for a particular protein. As is known in the art, possible introns interrupting this portion of the DNA are not part of the CDS. A reading frame is herein understood as the division of nucleotides in a nucleic acid into a set of consecutive, non-overlapping, triplets. Hence, a nucleic acid comprises three reading frames that can be read in a 5' to 3' direction, each reading frame beginning from a different nucleotide in a triplet. In a duplex DNA molecule, an additional three reading frames may be read from the other, complementary strand in the 5' to 3' direction. A duplex DNA molecule thus contains six reading frames. Furthermore, a frame shift is herein defined as a shift in the reading frame, i.e. caused by the insertion or deletion of a number of nucleotides that is not divisible by three. Alternatively, in the case the number of nucleotides that is deleted or introduced is (a multiple of) 3, the reading frame thus does not shift, i.e. the sequence of the reading frame remains in frame. A frame shift may result in a different translation of the CDS. It further is understood herein that a frameshift mutation is not the same as a single-nucleotide polymorphism in which a nucleotide is replaced, rather than inserted or deleted. A frameshift mutation may cause the reading of the codons after the mutation to code for different amino acids. It is to be understood herein that the CDS is a continuous stretch of codons (triplets), preferably starting with a start codon and ending with a stop codon in the same reading frame. When referring to a triplet in the context of a CDS, the words triplet and codon are used interchangeably herein.

The Altered Coding Sequence

In the method of the invention, a first nuclease cleaves the DNA generating a first indel at a first location and a second nuclease cleaves the DNA generating a second indel at a second location. It is to be understood herein that the second location is downstream (i.e. 3' as regarded from the coding strand perspective) of the first location. According to the method of the invention, the reading frame is not altered after the second location. Similarly, the reading frame is also not altered before the first location. In other words, the coding sequence after (downstream of) the second indel remains in the same reading frame as before (upstream of) the first indel.

Hence, the CDS is altered in between the first location and the second location, preferably the CDS is only altered in between the first location and the second location. The altered CDS starts with the indel created at the first location up to and including the indel created at the second location.

In an embodiment, the first indel is generated at a first location and the second indel is generated at the second location in the same CDS. Put differently, the first indel and second indel are generated in a single CDS, thus in one portion of the DNA that is composed of one or more subsequent exons that together code for a particular protein.

In the context of the invention, the resulting indels at the first and second position balance each other in the sense that the net result of inserted or deleted nucleotides within the CDS and caused by these two indels numbers 0, 3 or any plural of three. This may be achieved by a total introduction of nucleotides that is 0, 3 or any plural of three. Alternatively, the total of deleted nucleotides is 0, 3 or any plural of three. Preferably, the total of introduced nucleotides is preferably 0, 3, 6, 9 or 12 and/or the total of deleted nucleotides is preferably 0, 3, 6, 9 or 12.

The total of introduced nucleotides is to be understood herein as the total of nucleotides that are introduced at the first location and at the second location, i.e. the sum of the nucleotides introduced/deleted at the first and second location. For example, one nucleotide may be introduced at the first location (+1) and two nucleotides may be introduced at the second location (+2), which is annotated as (+1/+2). The total of introduced nucleotides in this example is 3. In another example, one nucleotide is deleted at the first location (−1) and one nucleotide is added at the second location (+1). The total number of added/deleted nucleotides in this example (−1/+1) is 0.

Optionally, the reading frame is altered in between the first location and the second location. Within this embodiment, the reading frame is altered after the first and second location if the DNA is cleaved with respectively only the first nuclease or only the second nuclease.

It is further to be understood herein that the unaltered reading frame is identical to the reading frame before the duplex DNA was cleaved with the first and/or second nuclease. Likewise, it is to be understood herein that the altered reading frame differs (i.e. is not identical) from the reading frame before the duplex DNA was cleaved with the first and/or second nuclease.

All triplets in the altered reading frame located in between and including the first and second indel may be different in comparison to the reading frame before the DNA was cleaved with the first and/or second nuclease. However, it is also part of the invention that not all triplets in between the first and second location are modified. The altered reading frame may for example comprise at least about 1, 2, 3, 4, 5, 6, 7, 8, 9, 10, 15, 20, 25, 30, 35, 40, 45 or 50 modified triplets. Alternatively, the altered reading frame may comprise at most about 1, 2, 3, 4, 5, 6, 7, 8, 9, 10, 15, 20, 25, 30, 35, 40, 45 or 50 modified triplets. More preferably, the altered reading frame may comprise about 1, 2, 3, 4, 5, 6, 7, 8, 9, 10, 15, 20, 25, 30, 35, 40, 45 or 50 modified triplets.

Similarly, the triplets of the altered CDS (the CDS starting with the first indel up to and including the second indel) may be 100% different in comparison to the triplets of the CDS before the DNA was cleaved with the first and/or second nuclease, i.e. all triplets between the first and second location are altered. Similarly, a 50% difference is used herein to indicate that 50% of the triplets between the first and second location are altered. The altered CDS may for example differ at least about 5, 10, 15, 20, 35, 30, 35, 40, 45, 50, 55, 60, 65, 70, 75, 80, 85, 95, or 100% with the non-cleaved DNA. Alternatively, the triplets of the altered CDS may differ at most about 5, 10, 15, 20, 35, 30, 35, 40, 45, 50, 55, 60, 65, 70, 75, 80, 85, 95, or 100% with the non-cleaved DNA. Preferably, the triplets of the altered CDS may differ about 5, 10, 15, 20, 35, 30, 35, 40, 45, 50, 55, 60, 65, 70, 75, 80, 85, 95, or 100% with the non-cleaved DNA.

In a further preferred embodiment, the first and second nuclease cleave both strands of the DNA at specific locations. The DNA repair mechanism that subsequently repairs the generated double-stranded breaks is however error-prone. As a consequence, upon repairing the DNA one or more nucleotides may be newly added or one or more nucleotides of the original DNA sequence may be removed. Put differently, the repair of the double-stranded DNA breaks may result in the generation of indels (the insertion or deletion of nucleotides). As a consequence of the introduction of indels, the reading frame may shift.

The CDS is altered by the method of the invention by introducing or deleting at least one nucleotide at the first location and by introducing or deleting at least one nucleotide at the second location. Preferably, the CDS is altered by introducing at least one base pair at the first location and deleting at least one base pair at the second location, or preferably the CDS is altered by deleting at least one base pair at the first location and introducing at least one base pair at the second location.

More preferably, at the first location 1, 2, 3, 4, 5 or 6 nucleotides may be introduced or 1, 2, 3, 4, 5 or 6 nucleotides may be removed. In addition, preferably at the second location 1, 2, 3, 4, 5 or 6 nucleotides may be introduced or 1, 2, 3, 4, 5 or 6 nucleotides may be removed. It is preferred that at the first location 1 or 2 nucleotides may be introduced or 1 or 2 nucleotides may be removed. In addition, preferably at the second location 1 or 2 nucleotides may be introduced or 1 or 2 nucleotides may be removed.

Within the context of the present invention, the total sum of introduced/deleted nucleotides is always 0, 3 or any plural of 3 to prevent a frame shift after the second location.

In a preferred embodiment, the total sum of introduced/deleted nucleotides is 0, thereby rendering the physical position of the encoded amino acids of the CDS after the second indel unchanged. Preferably, the indel at the first location causes a frame shift (i.e. encompasses an insertion or deletion of 1 or more nucleotides with the exception of 3 or any plural of 3), which is then corrected by the indel at the second location that causes a frame shift which restores the original reading frame downstream of the indel at the second location. However it is also contemplated within the invention that the number of introduced/deleted nucleotides at the first location is 3 or any plural of 3 and the number of introduced/deleted nucleotides at the second the second location is 3 or any plural of 3. In this scenario the CDS will be altered, even though there was no frame shift after the first indel.

The method of the invention results in a modification/alteration of the CDS due to an introduction of an indel at the first and second location, wherein the altered CDS is the CDS starting with the first indel up to and including the second indel. The length of the altered CDS may have nearly or precisely the same length as the unaltered/original CDS. A frame shift encompassing a substantial part of the original CDS may often result in a non-functional protein. Instead, the method of the invention allows also for the modification of short stretches of amino acids within a single protein. Therefore in a preferred embodiment of the invention, the length of the altered CDS (starting with the first indel up to and including the second indel) is between about 3-750 nucleotides (nt), 3-600 nt, 3-450 nt, 3-300 nt, 3-150 nt, 3-75 nt, 3-60 nt, 3-45 nt, 3-30 nt or 3-15 nt. In a further preferred embodiment of the invention, the length of the altered CDS (starting with the first indel up to and including the second indel) is between about 6-750 nucleotides (nt), 6-600 nt, 6-450 nt, 6-300 nt, 6-150 nt, 6-75 nt, 6-60 nt, 6-45 nt, 6-30 nt or 6-15 nt. In a further preferred embodiment of the invention, the length of the altered CDS (starting with the first indel up to and including the second indel) is between about 9-750 nucleotides (nt), 9-600 nt, 9-450 nt, 9-300 nt, 9-150 nt, 9-75 nt, 9-60 nt, 9-45 nt, 9-30 nt or 9-15 nt. In a further preferred embodiment of the invention, the length of the altered CDS (starting with the first indel up to and including the second indel) is between about 12-750 nucleotides (nt), 12-600 nt, 12-450 nt, 12-300 nt, 12-150 nt, 12-75 nt, 12-60 nt, 12-45 nt, 12-30 nt or 12-15 nt. In a further preferred embodiment of the invention, the length of the altered CDS (starting with the first indel up to and including the second indel) is between about 15-750 nucleotides (nt), 15-600 nt, 15-450 nt, 15-300 nt, 15-150 nt, 15-75 nt, 15-60 nt, 15-45 nt, 15-30 nt. Similarly, the length, preferably the total length, of the altered CDS (starting from the first indel up to and including the second indel) is preferably between about 1-1000 codons, 1-500 codons, 1-300 codons, preferably between about 1-250, 1-200, 1-150, 1-100, 1-50, 1-25, 1-20, 1-15, 1-10 or 1-5 codons. The length, preferably the total length, of the altered CDS is between about 2-1000 codons, 2-500 codons, 2-300 codons, preferably between about 2-250, 2-200, 2-150, 2-100, 2-50, 2-25, 2-20, 2-15 or 2-10 codons. The length, preferably the total length, of the altered CDS is between about 3-1000 codons, 3-500 codons, 3-300 codons, preferably between about 3-250, 3-200, 3-150, 3-100, 3-50, 3-25, 3-20, 3-15 or 3-10 codons. The length, preferably the total length, of the altered CDS is between about 4-1000 codons, 4-500 codons, 4-300 codons, preferably between about 4-250, 4-200, 4-150, 4-100, 4-50, 4-25, 4-20, 4-15 or 4-10 codons. The length, preferably the total length, of the altered CDS is between about 5-1000 codons, 5-500 codons, 5-300 codons, preferably between about 5-250, 5-200, 5-150, 5-100, 5-50, 5-25, 5-20, 5-15 or 5-10 codons. Preferably, the length of the altered CDS is about 1, 2, 3, 4, 5, 6, 7, 8, 9, 10, 11, 12, 13, 14, 15, 20, 25, 30, 35, 40, 50, 100, 150, 200, 250, 300, 500 or 1000 codons.

In a particularly preferred embodiment, the altered CDS does not comprise a stop codon, i.e. a codon that signals (in mRNA) the termination of translation into proteins. Hence preferably the modified CDS does not comprise a triplet having in a 5' to 3' direction the sequence TAG (amber), TGA (opal/umber) or TAA (ochre).

In a further preferred embodiment, the resulting CDS of the method of the invention comprising the targeted alteration (i.e. the altered CDS) encodes for a protein product. More precisely, the resulting CDS preferably maintains the potential to be translated into a protein. Preferably, the protein translated from the resulting CDS is a functional protein, e.g. a protein having a biological activity. The biological activity can be the same or a different biological activity as compared to the biological activity of the protein translated from the starting material comprising the unaltered CDS. Preferably, the biological activity of the protein translated from the resulting CDS may be increased or decreased as compared to the biological activity of the protein translated from the unaltered CDS.

In a further preferred embodiment, the method of the invention is an ex vivo method, preferably the method is an in vitro method. The method of the invention may be a method for treatment of the human or animal body. Preferably, the method is not a method for treatment of the human or animal body.

Analysing the Altered Coding Sequence

In an embodiment, the method of the invention comprises a step of analysing or identifying the altered coding sequence. The nucleotide sequence surrounding the first location and/or the sequence surrounding the second location can be analysed. Preferably at least the indel generated at the first location and the indel generated at the second location is determined. The complete nucleotide sequence of at least the altered CDS can be analysed. In addition, the complete sequence of at least the CDS can be analysed.

Analysing the nucleotide sequence can be performed using any conventional method known in the art. As a non-limiting example, the nucleotide sequence can be analysed using restriction enzyme analysis, electrophoresis, and/or sequencing, such as, but not limited to sanger sequencing or high-throughput sequencing.

Analysing the nucleotide sequence preferably results in the identification of the nucleotide sequence.

Alternatively or in addition, the protein transcribed from the resulting CDS (i.e. comprising the targeted alteration) can be analysed using any conventional method known in the art. Such analysis can be based on the protein function or structure. As a non-limiting example of structural analysis, the amino acid composition of the transcribed protein be identified, e.g. using chromatographic separation of the hydrolysed amino acids. Protein function can be analysed by any suitable functional analysis assay depending on the nature of the protein that is encoded by CDS altered by the method of the invention. Altering the CDS by the method of the invention may result in loss of protein function, i.e. an abolished or decreased protein function, or gain of protein function, i.e. an increased or newly created protein function. Optionally, such protein function may be analysis in vitro, preferably after purification of the protein from its natural or cellular environment, or in vivo, preferably in its natural or cellular environment, preferably as present in the cell comprising the altered duplex DNA derived from the method of the invention, or as present in any cell, tissue or organism derived therefrom.

Analysing the protein function in such cell, tissue or organism can be done by analysing the phenotype of such cell, tissue or organism.

Altering part of a CDS may lead to a modified phenotypic characteristic, preferably as compared to the same cell, tissue or organism not comprising the altered CDS. As a non-limiting example, altering part of a specific CDS in a plant gene can result in an altered phenotypic plant characteristic. A preferred phenotypic plant characteristic can be selected from the group consisting of plant development, plant growth, yield, biomass production, plant architecture, plant biochemistry, plant physiology, metabolism, herbicide resistance, survival capacity and stress tolerance. Alternatively or in addition, the plant characteristic is selected from the group consisting of DNA synthesis, DNA modification, endoreduplication, cell cycle, cell wall biogenesis, transcription regulation, signal transduction, storage lipid mobilization, and photosynthesis. Preferably, the altered plant characteristic results in an economically more beneficial plant phenotype.

In an embodiment, the altered CDS as defined herein and/or the cell, tissue or organism comprising or expressing the altered CDS as defined herein can be isolated. Preferably, the altered CDS as defined herein can be isolated or separated from at least the unaltered CDS as defined herein. In addition or alternatively, the altered CDS as defined herein can be isolated or separated from at least a modified CDS, wherein the modified CDS docs not remain in the same reading frame before the first and/or after the second indel. In addition or alternatively, the altered CDS as defined herein can be isolated or separated from at least a modified CDS, wherein the modified CDS comprises a stop codon.

Preferably, a cell, tissue or organism comprising the altered CDS as defined herein can be isolated or separated from at least the cell, tissue or organism comprising unaltered CDS as defined herein. In addition or alternatively, a cell, tissue or organism comprising the altered CDS as defined herein can be isolated or separated from at least a cell, tissue or organism comprising modified CDS, wherein the modified CDS does not remain in the same reading frame before the first and/or after the second indel. In addition or alternatively, the cell, tissue or organism comprising the altered CDS as defined herein can be isolated or separated from at least a cell, tissue or organism comprising the modified CDS, wherein the modified CDS comprises a stop codon.

Cell Type

The skilled person understands that the method of the invention is not limited to a certain cell type. In particular, the method of the invention as disclosed herein can be applied to dividing as well as non-dividing cells. The cell may be transgenic or non-transgenic. Furthermore, the method of the invention can be applied to cells derived from an animal, a plant or a fungus, or can be a bacterial cell or a yeast cell. Preferred cells for use in the method of the invention are animal or plant cells. A preferred animal cell is a mammalian cell, preferably a non-human primate cell or a human cell. A plant cell can for example be obtainable from plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grains and the like.

In a preferred embodiment, the plant cell is a plant protoplast. The skilled person is aware of methods and protocols for preparing and propagating plant protoplasts, see for example Plant Tissue Culture (ISBN: 978-0-12-415920-4, Roberta H. Smith). The plant protoplasts for use in the method of the current invention can be provided using common procedures used for the generation of plant cell protoplasts (e.g. the cell wall may be degraded using cellulose, pectinase and/or xylanase).

Plant cell protoplasts systems have for example been described for tomato, tobacco and many more (*Brassica napus, Daucus carota, Lactucca sativa, Zea mays, Nicotiana benthamiana, Petunia hybrida, Solanum tubcrosum, Oryza sativa*). The present invention is generally applicable to any protoplast system, including those, but not limited to, the systems described in any one of the following references: Barsby et al. 1986, Plant Cell Reports 5(2): 101-103; Fischer et al. 1992, Plant Cell Rep. 11(12): 632-636; Hu et al. 1999, Plant Cell, Tissue and Organ Culture 59: 189-196; Niedz et al. 1985, Plant Science 39: 199-204; Prioli and Söndahl, 1989, Nature Biotechnology 7: 589-594; S. Roest and Gilissen 1989, Acta Bot. Neerl. 38(1): 1-23; Shepard and Totten, 1975, Plant Physiol. 55: 689-694; Shepard and Totten, 1977, Plant Physiol. 60: 313-316, which are incorporated herein by reference.

The plant cell is preferably obtainable from a crop plant such as a monocot or dicot or of a crop or grain plant such as cassava, corn, sorghum, soybean, wheat, oat or rice. A crop plant is plant species which is cultivated and bred by humans. A crop plant may be cultivated for food purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork and the like.

The plant cell may also be of an alga, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinacia*; plants of the genus *Capsicum*; plants of the genus *Solanum*).

In another preferred embodiment, the cell is obtainable from a plant selected from the group consisting of asparagus, barley, blackberry, blueberry, broccoli, cabbage, canola, carrot, cassava, cauliflower, chicory, cocoa, coffee, cotton, cucumber, eggplant, grape, hot pepper, lettuce, maize, melon, oilseed rape, pepper, potato, pumpkin, raspberry, rice, rye, sorghum, spinach, squash, strawberry, sugar cane, sugar beet, sunflower, sweet pepper, tobacco, tomato, water melon, wheat, and zucchini.

Preferably, the obtained plant cell comprising the targeted alteration is regenerated into a plant or descendent therefore. Therefore a preferred embodiment of the invention, the method further comprises a step of regenerating a plant or descendent thereof comprising the targeted alteration.

Site-Specific Nucleases

The method of the invention comprises a step of exposing the DNA to at least two site-specific nucleases. The skilled person understands that any site-specific nuclease is suitable for use in the method of the invention. Preferably, the site-specific nuclease is a site-specific restriction endonuclease or a site-specific nicking endonuclease.

A restriction endonuclease is to be understood herein as an endonuclease that hydrolyses both strands of the duplex at the same time to introduce a double strand break in the DNA. A nicking endonuclease is an endonuclease that hydrolyses only one strand of the duplex to produce DNA molecules that are "nicked" rather than cleaved. Preferably the site-specific nuclease is a site-specific restriction endonuclease. Alternatively, the nuclease may be a nicking endonuclease. Preferably at least two nicking nucleases may be used in the method of the invention, whereby the at least two nicking endonuclease preferably recognize and nick opposite strands in the same duplex DNA such that a double stranded break is created at the first or second location.

The location of the double-stranded break is determined by the site-specific nuclease, sometimes in combination with a guide RNA as detailed herein below. It is well-known in the art how to design a site-specific nuclease to ensure that the nuclease cleaves at a specific location in the duplex DNA. Hence, the skilled person knows how to design a site-specific nuclease to cleave the DNA at the predetermined first or second location. The cleavage site (the first location and the second location) is determined by the sequence that is targeted by the nuclease, i.e. the target sequence. Preferably, the target sequence refers to a duplex DNA molecule comprising a sequence greater than 8 nucleotides in length but less than 201 nucleotides in length. Preferably, the target sequence is between 8 to 30 bases. The target sequence is, in general, defined by the nucleotide sequence on one of the strands on the double-helical nucleic acid.

In a preferred embodiment, at least one of the nucleases is selected from the group consisting of a CRISPR nuclease, a TALEN, a zinc finger nuclease and a meganuclease. In a preferred embodiment at least one nuclease is a CRISPR nuclease. In some embodiments at least one nuclease is a TALEN.

TALENs (Transcription activator-like effector nucleases) are targetable nucleases and are used to induce single- and double-strand breaks into specific DNA sites, which are then repaired by mechanisms that may create indels at the cleavage site. The fundamental building block that is used to engineer the DNA-binding region of TALENs is a highly conserved repeat domain derived from naturally occurring TALEs encoded by *Xanthomonas* spp. proteobacteria. DNA binding by a TALEN is mediated by arrays of highly conserved 33-35 amino acid repeats that are flanked by additional TALE-derived domains at the amino-terminal and carboxy-terminal ends of the repeats. These TALE repeats specifically bind to a single base of DNA, the identity of which is determined by two hypervariable residues typically found at positions 12 and 13 of the repeat, with the number of repeats in an array corresponded to the length of the desired target nucleic acid, the identity of the repeat selected to match the target nucleic acid sequence.

In some embodiments, the target sequence in the nucleic acid is between 15 and 20 base pairs in order to maximize selectivity of the target site. Cleavage of the target nucleic acid typically occurs within 50 base pairs of TALEN binding. Computer programs for TALEN recognition site design have been described in the art. See, e.g., Cermak et al, Nucleic Acids Res. 2011 July; 39(12): e82.

Once designed to match the desired target sequence, TALENs can be expressed recombinantly and introduced into protoplasts as exogenous proteins, or expressed from a plasmid within the protoplast or administered as mRNA.

In a preferred embodiment, the nuclease may be a zinc finger nuclease. Zinc finger endonucleases combine a non-specific cleavage domain, typically that of FokI endonuclease, with zinc finger protein domains that are engineered to bind to specific DNA sequences. The modular structure of the zinc finger endonucleases makes them a versatile platform for creating site-specific double-strand breaks to the genome. As FokI endonuclease cleaves as a dimer, one strategy to prevent off-target cleavage events has been to design zinc finger domains that bind at adjacent 9 base pair sites. See also U.S. Pat. Nos. 7,285,416; 7,521,241; 7,361,635; 7,273,923; 7,262,054; 7,220,719; 7,070,934: 7,013,219: 6,979,539; 6,933,113; 6,824,978; each of which is herein incorporated by reference in its entirety.

In a preferred embodiment, the nuclease may be a meganuclease. The homing endonucleases, also known as meganucleases, are sequence specific endonucleases that generate double strand breaks in genomic DNA with a high degree of specificity due to their large (e.g., >14 bp) target sequence. While the specificity of the homing endonucleases for their target sites allows for precise targeting of the induced DNA breaks, homing endonuclease cleavage sites are rare and the probability of finding a naturally occurring cleavage site in a targeted gene is low. Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease. See e.g., U.S. Pat. Nos. 8,338,157.

In a further preferred embodiment, the site-specific nuclease is a CRISPR nuclease, such as CRISPR-Cas. The term CRISPR-nuclease, Cas, Cas-protein or Cas-like protein refers to CRISPR related proteins and includes but is not limited to CAS9, CSY4, nickases (e.g. Cas9_D10A, Cas9_H820A or Cas9_H839A), Mad7 and fusion proteins (e.g. Cas9 or Cas-like molecules fused to a further functional domain such as a heterologous nickase/endonuclease domain), and other examples, such as Cpf1 or Cpf1_R1226A and such as for example described in WO2015/006747, WO2018/115390 and U.S. Pat. No. 9,982,279, which are incorporated herein by reference. Mutants and derivatives of Cas9 as well as other Cas proteins can be used in the methods disclosed herein. Preferably, such other Cas proteins have endonuclease activity and are able to recognize a target nucleic acid sequence when in a cell in the presence of a gRNA that is engineered for recognition of the target sequence. The CAS-protein or CAS-like protein is preferable the CAS9 protein of Cpf1.

CAS or CAS-like protein may be, but is no limited to, selected from the group consisting of: Cas9 from *Streptococcus pyogenes* (e.g. UniProtKB—Q99ZW2), Cas9 from *Francisella tularensis* (e.g. UniProtKB—A0Q5Y3), Cas9 from *Staphylococcus aureus* (e.g. UniProtKB—J7RUA5), Cas9 from *Actinomyces naeslundii* (UniProtKB—J3F2B0), Cas9 from *Streptococcus thermophilus* (e.g. UniProtKB—G3ECR1; UniprotKB-Q03J16; Q03LF7), Cas9 from *Neisseria meningitidis* (e.g. UniProtKB—C9X1G5; UniProtKB—A11Q68); *Listeria innocua* (e.g. UniProtKB—Q927P4); Cas9 from *Streptococcus mutans* (e.g. UniProtKB—Q8DTE3); Cas9 from *Pasteurella multocida* (e.g. UniProtKB—Q9CLT2); Cas9 form *Corynebacterium diphtheriae* (e.g. UniProtKB—Q6NKI3); Cas9 from *Campylobacter jejuni* (e.g. UniProtKB—Q0P897), Cpf1 from *Francisella tularensis* (e.g. UniProtKB—A0Q7Q2), Cpf1 from *Acidaminococcus* sp. (e.g. UniProtKB—U2UMQ6), any orthologue thereof or any CRISPR associated endonuclease derived therefrom.

Preferred CRISPR-Cas for use in the method of the invention are CRISPR-Cas9 or CRISPR-Cpf1. In other embodiments, the Cas protein may be a homolog of Cas9 in which at least one of the RuvC, HNH, REC and BH domains is highly conserved.

A preferred Cas nuclease is Cas9. A CRISPR-Cas9 system contains three basic design components: 1) a Cas protein; 2) a crRNA; and 3) a trans-activating crRNA (tracrRNA). In a preferred embodiment, the tracrRNA and crRNA may be combined in a single chain chimeric RNA (single guide RNA/sgRNA/gRNA). The Cas9 protein is widely commercial available, as well as modified versions thereof (and which are also contemplated as CAS protein within the context of the current invention). The Cas9 protein has (endo)nuclease activity and is able to produce a specific DNA double strand break (DSB) at the target sequence. Indeed, it has been shown that the Cas9 protein (nuclease), tracrRNA and crRNA (the components of the CRISPR system) or the sgRNA (the chimeric fusion of the tracrRNA and crRNA) targeting a genomic sequence creates targeted DSBs at the genomic target sequence that is often misrepaired by the cellular DNA machinery, resulting in a small insertion or deletion (indel) (Feng et al. (2013) Cell Res. 1: 4; Li et al. (2013) Nat. Biotech. 10 31: 689-691; Nekrasov et al. (2013) Nat. Biotech. 31: 691-693; Shan et al. (2013) Nat. Biotech. 31: 686-688).

In another preferred embodiment, the CRISPR-nuclease is Cpf1. Cpf1 is a single RNA-Guided Endonuclease of a Class 2 CRISPR-Cas System (Cell (2015) 163(3):759-771). Notably, Cpf1 is a single crRNA-guided endonuclease and it utilizes a T-rich protospacer-adjacent motif. Unlike Cas9, which requires crRNA and tracrRNA to mediate interference, Cpf1-crRNA complexes alone may cleave target DNA molecules, i.e. without the requirement for any additional RNA species. Cpf1 may thus be used as an alternative CAS-protein.

The CRISPR system comprises basically two components: a "guide" RNA (gRNA) and a nonspecific CRISPR-associated endonuclease (e.g. Cas9 or Cpf1). The gRNA is a short RNA composed of a scaffold sequence necessary for Cas-binding and a user-defined nucleotide "targeting" sequence which defines the genomic target to be modified. Thus, one can change the genomic target of the CRISPR-nuclease (e.g. Cas9 or Cpf1) by simply so changing the targeting sequence present in the gRNA. A guide RNA (gRNA) may be a crRNA hybridized to a tracrRNA, or a single chain guide RNA as described e.g. Jinek et al. (2012, Science 337: 816-820) when used in combination with e.g. the Cas9 nuclease. The gRNA is further to be understood to be a single RNA-guide (crRNA) such as for use with Cpf-1. Hence, the gRNA is the RNA molecule that directs the nuclease to a specific target sequence in the duplex DNA.

The guide RNA, when used in combination with e.g. Cas9, may be a fusion between a crRNA and a tracrRNA. It is however also contemplated within the invention that instead of a single sgRNA, a tracrRNA and a crRNA as separate RNA molecules can be used in combination with e.g. Cas9. However in a preferred embodiment, the CRISPR-nuclease is used in combination with a single (e.g. chimeric) gRNA.

As clarified above, the CRISPR system requires at least two basic components, a CRISPR nuclease and a guide RNA. The skilled person knows how to prepare the different components of the CRISPR-nuclease system. In the prior art numerous reports are available on its design and use. See for example the recent review by Haeussler et al (J Genet Genomics. (2016)43(5):239-50) on the design of sgRNA and its combined use with the CAS protein CAS9 (originally obtained from *S. pyogenes*).

Hence, in a preferred method of the invention at least one of the nucleases is a CRISPR nuclease and preferably the method further comprises exposing the duplex DNA to at least one guide RNA. The guide RNA directs the CRISPR nuclease to the first location or to the second location. Hence, the at least one guide RNA comprises a first guide sequence for targeting the first nuclease to the first location in the duplex DNA or the guide RNA comprises a second guide sequence for targeting the second nuclease to the second location in the duplex DNA.

Preferably, at least one of the first and second nuclease of the method of the invention does not cleave any of the PAM and target sequence for binding of the guide RNA, or at least the nucleotides essential for efficient binding of the guide RNA to the target sequence, of the respective other nuclease of the method of the invention. As the nucleases may exert their binding and cleaving event consecutively, the method of the invention still works if only one of the first and second nuclease of the method of the invention cleaves the PAM or nucleotides essential for efficient binding of the guide RNA to the target sequence of the respective other nuclease.

Preferably, the first nuclease does not cleave the DNA at a location that is required by the second guide RNA to target the second nuclease to the second location. Alternatively or in addition, the second nuclease does not cleave the DNA at a location that is required by the first guide RNA to target the first nuclease to the first location.

In an embodiment, the first nuclease does not cleave at least one of:
  the PAM sequence required for targeting the second nuclease to the second location; and
  the DNA target sequence for targeting the second nuclease to the second location.

Preferably, the first nuclease at least does not cleave the PAM sequence required for targeting the second nuclease to the second location.

In addition or alternatively, the second nuclease does not cleave at least one of:
- the PAM sequence required for targeting the first nuclease to the first location; and
- the DNA target sequence for targeting the first nuclease to the first location.

Preferably, the second nuclease at least does not cleave the PAM sequence required for targeting the first nuclease to the first location.

The skilled person knows how to design the guide RNAs such that the first or second nuclease does not cleave the DNA at a location that is required for targeting respectively the second or first nuclease to the DNA.

Below a non-limiting example is provided for the Cas9 nuclease targeting both the first and second location. This non-limiting example thus concerns a site-specific nuclease that cleaves upstream of the PAM site. However, the person skilled in the art straightforwardly understands that similar calculations can be made for a site-specific nuclease that cleaves the DNA downstream of the PAM site, such as Cpf1 and MAD7, or combinations of different nucleases targeting the first and the second location respectively.

As a non-limiting example for e.g. the Cas9 nuclease targeting both the first and second location, the cleavage site of the nuclease may be located 3 nt upstream (5') of the PAM site. The PAM sequence may have a length of 3 nucleotides (e.g. NGG). The first guide RNA binds adjacent to a PAM site for targeting the first nuclease to the first location and the second guide RNA binds adjacent to a further PAM site for targeting the second nuclease to the second location. Hence, there should be at least two PAM sites present in the same CDS.

When the two PAM sites are located on the same strand, preferably the distance between the PAM site required for targeting the first nuclease and the PAM site required for targeting the second nuclease is at least 3 nt, i.e. the minimal distance between the PAM sites is preferably at least the same as the distance between the PAM site and the cleavage site.

Therefore in an embodiment wherein a first PAM site for targeting the first nuclease and a second PAM site for targeting the second nuclease are located on the same strand, the distance between the two PAM sites is at least the same as the distance between the downstream (3') PAM site and its cleavage site. The distance between the two PAM sites is preferably at least about 3, 4, 5, 6, 7, 8, 9, 10, 11, 12, 13, 14, 15, 17, 20, 23, 25 or at least about 30 nucleotides. Preferably, the distance between the two PAM sites is at least 5 nt.

As a further non-limiting example for e.g. the Cas9 nuclease, if the PAM sites are located on opposite strands and one PAM site is located upstream (5') of the other PAM site (i.e. the 5' ends of the PAM sites are closer together than the 3' ends of the PAM sites), the distance between the two PAM sites is preferably at least the difference between the PAM site and the cleavage site, e.g. 3 nt and the length of the sequence of the target DNA sequence essential for binding of the guide RNA, e.g. at least 12 or at least 13, 14, 15, 16, 17, 18, 19, or 20 nucleotides. The DNA target sequence may have length of e.g. 20 nucleotides and can be present directly upstream and complementary to the strand comprising the PAM sequence. When the PAM sites are located on opposite strands and one PAM site is located 5' of the other PAM site, the distance between the PAM sites is preferably at least 15 nucleotides, or at least 16, 17, 18, 19, 20, 21, 22 or 23 nucleotides, This distance can be calculated as the distance between the PAM site and the cleavage site (3 nt) plus the length of the target sequence essential for binding of the guide RNA (at least 12 nt, or at least 13, 14, 15, 16, 17, 18, 19, or 20 nt).

Therefore in an embodiment wherein a first PAM site for targeting the first nuclease and a second PAM site for targeting the second nuclease are located on opposite strands and one PAM site is located upstream (5') of the other PAM site (i.e. the 5' ends of the two PAM sites are closer together than the 3' ends of the PAM sites), the distance between the two PAM sites is preferably at least the distance between the PAM site and its cleavage site. Preferably, the distance between the two PAM sites is preferably at least the distance between the PAM site and the cleavage site (3 nt) plus the length of the target sequence (20 nt). Preferably, the distance between the two PAM sites is at least about 20, 25, 30, 35, 40, 45 or about 50 nucleotides.

As a further non-limiting example for e.g. the Cas9 nuclease, if the PAM sites are located on opposite strands and one PAM site is located downstream (3') of the other PAM site (i.e. the 3' ends of the PAM sites are closer together than the 5' ends of the PAM sites), there preferably is not minimum distance between the PAM sites, as the PAM sites are now located downstream of each other, while in this non-limiting example, the Cas9 cleavage site is located upstream of the PAM site. Hence, the nuclease does not cleave at least one of the other PAM sites or DNA target sequences.

As indicated above, similar calculations can be made for a site-specific nuclease that cleaves downstream of the PAM site or for combinations of nucleases. For an example wherein both nucleases of the method of the invention cleave downstream of the PAM site, in an embodiment wherein a first PAM site for targeting the first nuclease and a second PAM site for targeting the second nuclease are located on the same strand, the distance between the two PAM sites is at least the same as the distance between the upstream (5') PAM site and its cleavage site.

In an embodiment, the distance between the PAM sites, preferably irrespective of whether the nuclease cleaves the DNA upstream or downstream of the PAM site is at least about 3, 4, 5, 6, 7, 8, 9, 10, II, 12, 13, 14, 15, 16, 17, 18, 19, 20, 21, 23, 23, 24, 25, 30, 35, 40, 45 or at least about 50 nucleotides.

In a further preferred embodiment, at least one of the nucleases is a CRISPR nuclease and the method further comprises exposing the duplex DNA to
  i) a first guide RNA that comprises a first guide sequence for targeting the first nuclease to the first location in the duplex DNA; and
  ii) a second guide RNA that comprises a second guide sequence for targeting the second nuclease to the second location in the duplex DNA.

In a further preferred embodiment, the at least one CRISPR nuclease is Cas9 or Cpf1. Hence, the first location may be cleaved with a CRISPR-Cas9 nuclease or the first location may be cleaved with a CRISPR-Cpf1 nuclease. Similarly, the second location may be cleaved with a CRISPR-Cas9 nuclease or the second location may be cleaved with a CRISPR-Cpf1 nuclease. Furthermore the first and second location may be cleaved by the same (type of) CRISPR-nuclease, e.g. both locations may be cleaved with either CRISPR-Cas9 or CRISPR-Cpf1. Alternatively, the first and second location may be cleaved by different (types of) CRISPR-nucleases, e.g. one of the locations may be cleaved with Cas9 and the other location may be cleaved with Cpf1.

In a further preferred embodiment, at least one of the nucleases is selected from the group consisting of a zinc finger nuclease, a meganuclease, and a TALEN. The invention contemplates the use of different types of site-specific nucleases to cleave the duplex DNA, for example, but not limited to, using a combination of a CRISPR-nuclease and a TALEN. Preferably, the nucleases used in the method of the invention are the same type of nuclease, for example, both the first and second location is cleaved by a CRISPR-nuclease, a zinc finger nuclease, a meganuclease or a TALEN.

Preferably, at least two site-specific nucleases cleave the DNA at least at two locations within the same CDS. In addition, the DNA may also be cleaved at more than two locations with the same CDS. As a non-limited example, the DNA may be cleaved at three locations within the same CDS, generating an indel at the first, second and third location within the CDS, and wherein the CDS before the first indel and after the third indel remain in the same reading frame. Within this embodiment, the reading frame between the first and second indel and between the second and third indel may be shifted. Similarly, the same CDS may be cleaved at e.g. four, five, six, seven or eight locations, generating indels at each location and wherein the reading frame after respectively the fourth, fifth, sixth, seventh or eighth location remains in frame with the reading frame before the first location, while the reading frame between the first and last indel may be shifted.

Alternatively, the duplex DNA may be cleaved at more than two locations within the same CDS whereby an indel is generated at each location, such that in between the first location and the last location a part of the reading frame is shifted and a part of the reading frame remains in frame with the CDS before the first indel. As a non-limiting example, the first indel may generate a frame shift, which is corrected by the second indel. Subsequently, an indel at the third location generates a new frame shift which is corrected by the indel at the fourth location. The generation of several frame shifts within a single reading frame as exemplified above, may be useful when targeted alterations at more than one part within the same reading frame is desired. Using the method of the invention, at least 1, 2, 3 or 4 predetermined parts of the same CDS can altered, preferably by introducing at least 1, 2, 3 or 4 times a frame shift, using respectively at least 2, 4, 6 or 8 site-specific nucleases. It is to be understood herein, the optionally the at least 1, 2, 3 or 4 predetermined parts of the same CDS are within the same or within different exons. Optionally each predetermined part is in a separate exon with the same CDS.

Hence, in a preferred embodiment, the duplex DNA is exposed to at least 2, 3, 4, 5, 6, 7 or 8 site-specific nucleases and wherein the at least 2, 3, 4, 5, 6, 7 or 8 site-specific nucleases cleave the duplex DNA of the same CDS. Preferably, the duplex DNA is exposed to two, three or four site-specific nucleases and wherein the two, three or four site-specific nucleases cleave the duplex DNA of the same CDS. More preferably, the duplex DNA is exposed to two or three site-specific nucleases and wherein the two or three site-specific nucleases cleave the duplex DNA of the same CDS.

Introducing Site-Specific Nucleases

The site-specific nucleases, and in a preferred embodiment where the site-specific nuclease is a CRISPR-nuclease also the guide RNA, may be introduced into the cell using any conventional method known in the art. As non-limiting examples, the introduction of the site-specific nuclease (and guide RNA) in the cell may constitute a transient expression from a plasmid vector, direct delivery of the protein, direct delivery of the mRNA into a cell and/or stable integration of the DNA coding for the protein and/or guide RNA into the genome of the cell. The site-specific nuclease protein may contain one or more nuclear localization signal sequences (NLS), mutations, deletions, alterations or truncations. In addition, the site-specific nuclease encoding genes may be codon optimized, e.g. for expression in higher plants, algae, yeast or animals and may be driven by either a constitutive, inducible, tissue-specific or species-specific promoter when applicable. Exemplary nuclease transcript termination and polyadenylation signals are either NosT, RBCT, HSP 18.2T or other gene specific or species-specific terminators. The nuclease gene cassettes or mRNA may contain introns, either native or in combination with gene-specific promoters and or synthetic promoters.

In a preferred embodiment, the cell is transformed with at least one of the site-specific nucleases, i.e. the nuclease protein is delivered directly into the cell. In a further embodiment, the cell is transformed with at least one of the guide RNAs. Preferably, the cell is transformed with at least one of the site-specific nucleases and at least one of the guide RNAs. Preferably, the cell is transformed with one site-specific CRISPR-nuclease and two guide RNAs.

In another preferred embodiment, the cell is transfected with a nucleic acid construct encoding at least one of the site-specific nucleases. In a further embodiment, the cell is transfected with a nucleic acid construct encoding at least one of the guide RNAs, preferably the nucleic acid construct encodes at least two guide RNAs. Preferably, the cell is transfected with a nucleic acid construct that encodes all guide RNAs that are used in the method for targeted alteration as described herein.

In addition, different nucleic acid constructs may be used in the method of the invention, whereby each nucleic acid construct encodes either a site-specific nuclease or a guide RNA. Alternatively, a single nucleic acid construct may encode at least two guide RNAs, or at least one guide RNA and at least one site-specific nuclease. In a preferred embodiment, the cell is transfected with a nucleic acid construct encoding at least two guide RNAs and a separate nucleic acid construct encoding at least one site-specific nuclease.

In a further preferred embodiment, the cells comprising the altered CDS as defined herein are separated from the cells not comprising the altered CDS. As a non-limiting example, the transformed or transfected cells may be multiplied and subsequently genotyped using any conventional method known in the art. In a preferred embodiment, the transformed/transfected cells may be genotyped using deep-sequencing technologies, such as Illumina or 454 sequencing.

The protein comprising the altered CDS may be further evaluated for an altered functionality using any conventional means.

There are many suitable approaches known in the art for delivering the nucleic acids (encoding the site-specific nuclease and/or (encoding) the guide RNAs) or the protein into the cell. The delivery system may for example constitute a viral-based delivery system or a non-viral delivery system.

Non-limiting examples of non-viral delivery systems include chemical-based transfection (e.g. using calcium phosphate, dendrimers, cyclodextrin, polymers, liposomes, or nanoparticles), non-chemical-based methods (e.g. electroporation, cell squeezing, sonoporation, optical transfection, protoplast fusion, impalefection, heat shock and hydrodynamic delivery), particle-based methods (e.g. a gene gun or magnet-assisted transfection) and bacterial-based delivery systems (e.g. agrobacterium-mediated delivery). Non-limiting examples of a viral delivery system includes lentivirus and adenovirus.

In a preferred embodiment, the nucleic acids and/or proteins are introduced into the cell using an aqueous medium, wherein the aqueous medium comprises PEG. Any suitable method can be used, preferably the medium has a pH value of between 5-8, preferably between 6-7.5. Next to the presence in the aqueous medium of the site-specific nuclease and optionally the gRNA, the medium comprises polyethylene glycol. Polyethylene glycol (PEG) is a polyether compound with many applications from industrial manufacturing to medicine. PEG is also known as polyethylene oxide (PEO) or polyoxyethylene (POE). The structure of PEG is commonly expressed as H—(O—CH2-CH2)n-OH. Preferably, the PEG used is an oligomer and/or polymers, or mixtures thereof with a molecular mass below 20,000 g/mol.

The aqueous medium comprising the population of e.g. plant cells preferably comprises 100-400 mg/ml PEG. So the final concentration of PEG is preferably between 100-400 mg/ml, for example, between 150 and 300 mg/ml, for example between 180 and 250 mg/ml. A preferred PEG is PEG 4000 Sigma-Aldrich no. 81240. (i.e. having an average Mn 4000 (Mn, the number average molecular weight is the total weight of all the polymer molecules in a sample, divided by the total number of polymer molecules in a sample.). Preferably the PEG used as a Mn of about 1000-10000, for example between 2000-6000).

In a further preferred embodiment, the aqueous medium comprising PEG does not comprise more than about 0.001%, 0.01%, 0.05%, 0.1%, 1%, 2%, 5%, 10% or 20% (v/v) glycerol. Preferably, the medium comprises less than about 0.001%, 0.01%, 0.05%, 0.1%, 1%, 2%, 5%, 10% or 20% (v/v) glycerol. In particular for the introduction of a site-specific nuclease protein, the aqueous medium comprises less than about 0.1% (for example, less than 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% (v/v) glycerol. Optionally, the aqueous medium comprising the population of plant cells is completely free of glycerol.

Preferably, the cell cycle of e.g. plant cells is synchronized when exposing the duplex DNA to the at least two site-specific inhibitors. The synchronization preferably takes places when the site-specific nuclease or nucleic acid encoding the site-specific nuclease is introduced into the cell as detailed herein. Synchronization is preferably performed by contacting the (plant) cell with a synchronizing agent.

Such method of synchronizing the cell cycle of the (plant) cell has been described in detail in European patent EP2516652, incorporated herein by reference. More particular, synchronizing the (plant) cells, for example, the plant protoplasts may be advantageous in certain embodiments of the invention to further enhance efficacy of the introduction of the alteration in the duplex DNA. Thus, in certain embodiments, the method comprises a step of synchronizing the cell cycle of the cell, preferably a plant cell.

The synchronization preferably takes places when the site-specific nuclease or nucleic acid encoding the site-specific nuclease is introduced into the cell as detailed herein, such that most of the (plant) cells will be in the same phase of the cell cycle when the duplex DNA is exposed to the site-specific nucleases as defined herein. This may be advantageous and increase the rate of introduction of the alteration in the duplex DNA.

Synchronizing the (plant) cell may be accomplished by any suitable means. For example, synchronization of the cell cycle may be achieved by nutrient deprivation such as phosphate starvation, nitrate starvation, ion starvation, serum starvation, sucrose starvation, auxin starvation.

Synchronization can also be achieved by adding a synchronizing agent to the (plant) cell. Preferably, the synchronizing agent is selected from the group consisting of aphidocolin, hydroxyurea, thymidine, colchicine, cobtorin, dinitroaniline, benefin, butralin, dinitramine, ethalfluralin, oryzalin, pendimethalin, trifluralin, amiprophos-methyl, butamiphos dithiopyr, thiazopyr propyzamide, tebutam DCPA (chlorthal-dimethyl), mimosine, anisomycin, alpha amanitin, lovastatin, jasmonic acid, abscisic acid, menadione, cryptogeine, hydrogenperoxide, sodiumpermanganate, indomethacin, epoxomycin, lactacystein, icrf 193, olomoucine, roscovitine, bohemine, staurosporine, K252a, okadaic acid, endothal, caffeine, MG 132, cycline dependent kinases and cycline dependent kinase inhibitors, as well as their target mechanism. The amounts and concentrations and their associated cell cycle phase are described for instance in "Flow Cytometry with plant cells", J. Dolezel c.s. Eds. Wiley-VCH Verlag 2007 pp 327 ff. Preferably, the synchronizing agent is aphidicolin and/or hydroxyurea.

Preferably, in the method of the invention, synchronizing the cell cycle synchronizes the (plant) cell in the S-phase, the M-phase, the G1 and/or G2 phase of the cell cycle.

Kit of Parts

In a second aspect, the invention pertain to a kit of parts, optionally for use in a method of the invention. Preferably, the kit of part comprises:
  a first container comprising a site-specific nuclease and/or a nucleic acid construct encoding the site-specific nuclease;
  a manual for targeted alteration of an ORF in duplex DNA in a cell according to the method as defined herein In a preferred embodiment, the kit of parts may further comprise a second container comprising at least two guide RNAs and/or at least one nucleic acid construct encoding at least one guide RNA, preferably at least two guide RNAs. Preferably, the guide RNAs are designed such that the first or second nuclease does not cleave the DNA at a location that is required for targeting respectively the second or first nuclease to the DNA.

In an embodiment, the first container may further comprise at least two guide RNAs and/or at least one nucleic acid construct encoding at least one guide RNA, preferably at least two guide RNAs. Preferably, the guide RNAs are designed such that the first or second nuclease does not cleave the DNA at a location that is required for targeting respectively the second or first nuclease to the DNA.

In a further preferred embodiment, the first container further comprises at least one of the following:
  i) at least two site-specific nucleases;
  ii) at least two nucleic acid constructs encoding the site-specific nucleases; and
  iii) a nucleic acid construct encoding at least two site-specific nucleases.

The reagents may be present in lyophilized form, or in an appropriate buffer. The kit may also contain any other component necessary for carrying out the present invention, such as buffers, pipettes, microtiter plates and written instructions. Such other components for the kits of the invention are known to the skilled person.

In a third aspect, the invention concerns the use of at least two site-specific nucleases as defined herein or a kit part as defined herein for the targeted alteration of an ORF in duplex DNA in a cell.

Products Obtainable by the Method of the Invention

In a fourth aspect, the invention therefore pertains to the altered DNA molecule obtained by the method of the invention, or any nucleic acid (e.g. mRNA transcribed from said altered DNA molecule) or nucleic acid construct derived therefrom. Such nucleic acid construct may be a chimer or vector further comprising homo- or heterogeneous translation and/or transcription regulatory sequences such as promoter sequence. Said altered DNA molecule may also be part of the genome of a cell.

The cell obtainable by the method of the invention may subsequently be propagated to e.g. obtain a culture of cells, (part of) an organism or any descendants thereof. Hence, the skilled person will understand that the method for targeted alteration of DNA in a cell may also find use as a method for the provision of a cell having a targeted alteration in a duplex DNA molecule. Preferably the cell is a plant cell. Similarly, the method of the invention may find use as a method for the provision of an organism, and a descendent thereof, comprising a targeted alteration in a duplex DNA molecule, wherein the alteration or modification is relative to the same organism not treated with the method according to the invention. Preferably the organism is a plant or plant part.

In a fifth aspect, the invention therefore pertains to a cell obtained or obtainable by the method of the invention. Preferably the cell is a plant cell or a protoplast. Preferably, the plant cell or plant protoplast is modified by comprising the targeted alteration when compared to a control, and wherein the control is plant cell or plant protoplast before the targeted alteration was introduced by the method of any of the preceding claims.

The plant cell or plant protoplast comprising the targeted alteration may subsequently be used to regenerate a plant or descendent thereof comprising the targeted alteration.

As a non-limiting example, using the method of the invention plants having an improved herbicide resistance were created. In particular, the method of the invention was used to introduce multiple indel mutations in the ALS genes of tomato. Briefly, tomato protoplasts were transfected with a plasmid vector encoding the *S. pyogenes* Cas9 ORF together with another plasmid vector carrying a cassette for the expression of three sgRNAs that target the region around the P184 codon of the ALS gene. There are a number of dominant ALS mutations known in the art that confer varying degrees of herbicide tolerance (Roux et al. supra). Many of the mutations that confer resistance to the SU class of herbicides are in or around the codon for P184 (e.g. P184L, P184R, P184Q etc). We therefore hypothesized that combinations of indel mutations in this region that would cause a frameshift around the P184 codon may also produce a herbicide resistant phenotype, and so we grew the transfected protoplasts in the presence of the SU herbicide chlorsulfuron.

Interestingly, we found that expression of only one of the guide RNAs in the protoplasts did not produce herbicide resistant calli, while we were able to isolate chlorsulfuron resistant calli when expressing the three guides simultaneously. The ALS genes of the resistant calli were sequenced and were found to have two indel mutations closely linked, the first one altered the protein reading frame while the second indel restored it. In all cases, both indels consisted of single base pair insertions or deletions. Due to this frameshift all of the codons between the two indels had been altered.

Using the method of the invention as detailed herein, we found that the ALS alleles in the resistant calli had the same combinations of indels, suggesting that only a subset of all of the possible indel combinations that result in a restoration of the reading frame also conferred herbicide resistance.

In a preferred embodiment, the invention therefore concerns a duplex DNA obtainable by the method of the invention, wherein the nucleic acid is modified by comprising a targeted alteration when compared to a control, and wherein the control is a DNA before the targeted alteration was introduced. The invention also concerns any nucleic acid or constructs derived therefrom.

In a preferred embodiment, the invention concerns a plant comprising the altered DNA obtainable by the method of the invention, wherein the plant is modified by comprising a targeted alteration when compared to a control, and wherein the control is a plant before the targeted alteration was introduced.

In a particularly preferred embodiment, the plant preferably comprises at least one altered ALS gene. Preferably, the altered ALS gene has at least about 60%, 65%, 70%, 75%, 80%, 85%, 90%, 95%, 98% 99% or 100% sequence identity with SEQ ID NO. 1 and wherein position 547-570 has at least about 85%, 90%, 95%, 98%, 99% or 100% sequence identity with any one of SEQ ID NO. 3-5. In addition or alternatively, the plant comprising the targeted alteration comprises at least one altered ALS gene having at least 60%, 65%, 70%, 75%, 80%, 85%, 90%, 95%, 98%, 99% or 100% sequence identity with SEQ ID NO. 2 and wherein position 541-564 has at least about 85%, 90%, 95%, 98%, 99% or 100% sequence identity with any one of SEQ ID NO. 3-5. Preferably, the plant comprising the targeted alteration has an improved herbicide resistance as compared to the control.

Preferably, the plant has an improved resistance for a herbicide selected from the group consisting of sulfonylureas (SU), imidazolinones (IM), triazalopyrimidines (TP), pyrimidinyl oxybenzoates (POBs) and sulfonylamino carbonyl triazolinones (SCTs). A preferred SU class herbicide is selected from the group consisting of amidosulfuron, azimsulfuron, bensulfuron-methyl, chlorsulfuron, cinosulfuron, flazasulfuron, flupyrsulfuron-methyl, foramsulfuron, Iodosulfuron, mesosulfuron, metsulfuron-methyl, nicosulfuron, rimsulfuron, sulfosulfuron, thifensulfuron-methyl, triasulfuron, tribenuron-methyl, triflusulfuron-methyl, imazamox, imazapyr, imazaquin and metosulam, preferably the herbicide is chlorsulfuron.

Preferably, the plant comprising the targeted alteration, comprises at least one altered ALS gene comprising a sequence having at least 80%, 85%, 90%, 95%, 96%, 97%, 98%, 99% or 100% sequence identity with a sequence having SEQ ID NO. 6, 7 or 8.

Preferably the plant obtainable by the method of the invention, wherein the plant is modified by comprising a targeted alteration, and wherein the plant comprises at least one altered ALS gene comprising a sequence having SEQ ID NO. 6, 7 or 8. Preferably, the plant comprises two altered ALS genes. Preferably, the plant comprises two altered ALS genes, wherein the altered ALS genes comprise a sequence having SEQ ID NO. 6, 7 or 8. Preferably, the first ALS gene comprises a sequence having SEQ ID NO. 6 or 7 and the second ALS gene comprises a sequence having SEQ ID NO. 8.

Preferably, the plant is selected from the group consisting of *Beta vulgaris, Linum usitatissimum Solanum tuberosum,*

Zea mays, Triticum spp., Triticum aestivum, Oryza saliva, Sorghum bicolor, Dioscorea spp., Manihot esculenta, Glycine max, Solanum Lycopersicon, Solanum lycopersicum, Gossypium hirsutum, Hordeum vulgare, Avena sativa, Secale cereale, and Brassica napus. Preferably, the plant is at least one of Beta vulgaris, Linum usitatissimum and Solanum Lycopersicon.

Preferably, the plant is a Solanum spp. preferably a Solanum Lycopersicon.

Using the method of the invention, a novel plant having an improved herbicide resistance was created. In a sixth aspect, the invention therefore relates to a plant having an improved herbicide resistance, wherein the plant has been genetically engineered to express at least one altered ALS protein.

Preferably, the ALS protein that is expressed has at least about 60%, 65%, 70%, 75%, 80%, 85%, 90%, 95%, 98% 99% or 100% sequence identity with SEQ ID NO. 9 and wherein position 183-192 has at least about 85%, 90%, 95%, 98%, 99% or 100% sequence identity with any one of SEQ ID NO. 11-13. In addition or alternatively, the plant comprising the targeted alteration expresses at least one altered ALS protein having at least about 60%, 65%, 70%, 75%, 80%, 85%, 90%, 95%, 98%, 99% or 100% sequence identity with SEQ ID No. 10 and wherein position 181-190 has at least about 85%, 90%, 95%, 98%, 99% or 100% sequence identity with any one of SEQ ID No. 11-13. Preferably, the plant expressing the altered ALS protein has an improved herbicide resistance as compared to compared to the same plant that does not express the altered ALS protein.

Preferably, the altered ALS protein is expressed de novo. The plant having the improved herbicide resistance may in addition express an endogenous unaltered ALS protein. Alternatively, the plant having the improved herbicide resistance does not express an endogenous unaltered ALS protein.

Preferably, the plant expresses at least one altered ALS protein, wherein the ALS protein comprises a sequence having at least about 80%, 85%, 90%, 95%, 96%, 97%, 98%, 99% or 100% sequence identity with a sequence having SEQ ID NO. 14, 15 or 16.

Preferably the plant expresses at least one altered ALS protein, wherein the ALS protein comprises a sequence having SEQ ID NO. 14, 15 or 16. Preferably, the plant comprises two altered ALS proteins, whereby each protein comprises a sequence having SEQ ID NO. 14, 15 or 16. Preferably, the plant comprises two altered ALS proteins whereby the first ALS protein comprises a sequence having SEQ ID NO. 14 or 15 and the second ALS protein comprises a sequence having SEQ ID NO. 16.

Preferably, the plant is selected from the group consisting of Solanum tuberosum, Zea mays, Triticum spp., Triticum aestivum, Oryza saliva, Sorghum bicolor, Dioscorea spp., Musa spp., Manihot esculenta, Glycine max, Solanum Lycopersicon, Solanum lycopersicum, Gossypium hirsutum, Hordeum vulgare, Avena saliva, Secale cereale, and Brassica napus. Preferably, the plant is a Solanum spp. preferably a Solanum Lycopersicon, and preferably a Solanum Lycopersicum.

Preferably, the plant of the invention has an improved resistance for a herbicide selected from the group consisting of sulfonylureas (SU), imidazolinones (IM), triazalopyrimidines (TP), pyrimidinyl oxybenzoates (POBs) and sulfonylamino carbonyl triazolinones (SCTs). A preferred SU class herbicide is selected from the group consisting of amidosulfuron, azimsulfuron, bensulfuron-methyl, chlorsulfuron, cinosulfuron, flazasulfuron, flupyrsulfuron-methyl, foramsulfuron, lodosulfuron, mesosulfuron, metsulfuron-methyl, nicosulfuron, rimsulfuron, sulfosulfuron, thifensulfuron-methyl, triasulfuron, tribenuron-methyl, triflusulfuron-methyl, imazamox, imazapyr, imazaquin and metosulam, preferably the herbicide is chlorsulfuron.

The preferred modifications are listed in Table 1 below.

TABLE 1

Sequences modified in ALS1 (nt SEQ ID NO. 1 and aa SEQ ID NO. 9) and ALS2 (nt SEQ ID NO. 2 and aa SEQ ID NO. 10)

| SEQ ID NO. | Description | Sequence |
|---|---|---|
| A. Nucleotide. SEQ ID NO. 17 (ALS1) or SEQ ID NO. 18 (ALS2) was replaced for SEQ ID NO. 3, 4 or 5 ||| 
| 17 | ALS 1 wt | GGTCAAGTGCCAAGGAGGATGATT |
| 18 | ALS 2 wt | GGTCAAGTGCCGAGGAGGATGATT |
| 3 | ALS2 mutant | GGTCAGTGCCGAGGAGGATTGATT |
| 4 | ALS2 mutant | GGTCAAAGTGCCAGGAGGATGATT |
| 5 | ALS 1 mutant | GGTCAAGTGCAAGGAGGATTGATT |
| B. Protein. SEQ ID NO. 19 (identical for ALS1 and ALS2) was replaced for SEQ ID NO. 11, 12 or 13 |||
| 19 | ALS 1 wt | GQVPRRMIGT |
| 19 | ALS 2 wt | GQVPRRMIGT |
| 11 | ALS2 mutant | GQCRGGLIGT |
| 12 | ALS2 mutant | GQSARRMIGT |
| 13 | ALS1 mutant | GQVQGGLIGT |

In a further aspect, the invention relates to a method for improving herbicide resistance in plants, comprising expressing at least one altered ALS protein in a plant, plant protoplast or plant cell, wherein the at least one ALS protein comprises an amino acid sequence having at least 70%, at least 80%, at least 85%, at least 90%, at least 95%, at least 98%, at least 99% or 100% sequence identity with any one of SEQ ID NOs: 14, 15 and 16.

The altered ALS protein can be encoded by, for example, a nucleic acid sequence having at least 70%, at least 80%, at least 85%, at least 90%, at least 95%, at least 98%, at least 99% or 100% sequence identity with any of SEQ ID NOs: 6, 7 and 8.

The method can comprise, for example, genetically engineering the plant, plant protoplast or plant cell to express the ALS protein. The method can comprise, for example, transforming a plant protoplast or plant cell with a vector or expression construct comprising a recombinant nucleic acid encoding the altered ALS protein. The method can comprise, for example, Agrobacterium-mediated transformation (e.g., contacting the plant protoplast or plant cell with an Agrobacterium strain comprising the vector or expression construct to introduce the recombinant nucleic acid into the plant protoplast or plant cell).

The method can further comprise, for example, regenerating the plant protoplast or plant cell into a plant. The method can further comprise, for example, producing seeds from the plant having improved herbicide resistance. The method can further comprise, for example, growing the seeds into plants having improved herbicide resistance.

The method can further comprise, for example, testing the plant, plant protoplast or plant cell for expression of the altered ALS protein. Methods for testing expression of the (altered) ALS protein include, but are not limited to, PCR analysis, sequencing of genomic DNA, sequencing of mRNA transcript, analyzing mRNA transcript levels (Northern-blot analysis), analyzing copy number (Southern blot analysis), etc.

The method can further comprise, for example, testing the plant, plant protoplast or plant cell for improved herbicide resistance. Methods for testing herbicide resistance are well known in the art and is exemplified in the example section below.

The method can further comprise, for example, producing progenies of the plant, plant protoplast or plant cell and selecting one or more progenies that express the at least one ALS protein of the invention. The method can further comprise, for example, producing progenies of the plant, plant protoplast or plant cell and selecting one or more progenies plants that have improved herbicide resistance.

Another aspect of the invention relates to a method for improving herbicide resistance in plants, comprising producing a plurality of plants, plant protoplasts or plant cells that have been genetically engineered to express the altered ALS protein, wherein the ALS protein comprises an amino acid sequence having at least 70%, at least 80%, at least 85%, at least 90%, at least 95%, at least 98%, at least 99% or 100% sequence identity with any of SEQ ID NOs: 14, 15 and 16, and screening the genetically-engineered plants, plant protoplasts or plant cells for improved herbicide resistance and selecting a plant, plant protoplast or plant cell having improved herbicide resistance.

A further aspect of the invention relates to a nucleic acid encoding an altered ALS protein, wherein the ALS protein has at least 70%, at least 80%, at least 85%, at least 90%, at least 95%, at least 98%, at least 99% or 100% sequence identity with any of SEQ ID NOs: 14, 15 and 16. In some embodiments, the nucleic acid sequence has at least 70%, at least 80%, at least 85%, at least 90%, at least 95%, at least 98%, at least 99% or 100% sequence identity with any of SEQ ID NOs: 6, 7 and 8.

Another aspect of the invention described herein pertains to a recombinant expression cassette comprising a nucleic acid comprising a nucleic acid sequence encoding an altered ALS protein operably linked to a promoter. In some embodiments, the expression cassette comprises a recombinant nucleic acid comprising a nucleic acid sequence encoding an altered ALS protein operably linked to a heterologous promoter.

In some embodiments, the promoter is active in plant cells. In some embodiments, the promoter is a heterologous promoter or is not operably linked to an ALS gene in naturally-occurring species. In some embodiments, the promoter is operably linked to an ALS gene in naturally-occurring species. In some embodiments, the promoter is a constitutive promoter. In some embodiments, the promoter is an inducible promoter.

Another aspect of the invention described herein pertains to a vector or expression construct comprising the expression cassette or nucleic acid as defined herein. In some embodiments, the vector or expression construct is configured for Agrobacterium-mediated transformation.

In a further aspect of the invention, provided is a use of the altered ALS protein, encoding nucleic acid or encoding expression cassette encoding said protein, for improving herbicide resistance in plants, preferably in a method of the invention as defined herein.

In an aspect, the invention further pertains to a composition comprising at least two site-specific nucleases for use in the method of the invention, or a construct encoding the same. In an embodiment, one or more of the site-specific nucleases are CRISPR nucleases as defined herein. The composition can further comprise one or more guide RNAs for targeting the one or more CRISPR nucleases to the first and second location as defined herein, or one or more constructs encoding the same. Preferably, the guide RNAs are designed such that the first or second nuclease does not cleave the DNA at a location that is required for targeting respectively the second or first nuclease to the DNA. In an embodiment, the composition further comprises a pharmaceutically acceptable carrier. In embodiment, the construct or constructs can be one or more gene therapy vectors.

In an aspect, the invention concerns a composition as defined herein for use as a medicament. Similarly, the invention pertains to a method of treatment, comprising a step of administering to a patient a composition as defined herein.

In a further aspect, the invention relates to a composition as defined herein for use in the treatment of a genetic disorder. The genetic disorder may be caused by the malfunctioning of one or more proteins, e.g. due to a partly aberrant CDS. The method as defined herein may target the aberrant CDS to specifically modify said part of the CDS.

In an aspect, the invention relates to a composition as defined herein for use in reducing the functionality of a protein associated with a disease. There are many proteins known that are crucial in disease development or severity. However, their knock out can be lethal. The method of the invention can reduce the protein functionality by specifically modifying only part of the CDS, resulting in a reduced functionality. Exemplary proteins are proteins known to play a role in at least one of cancer, Alzheimer and Parkinson.

All patent and literature references cited in the present specification are hereby incorporated by reference in their entirety. The following examples are offered for illustrative purposes only, and are not intended to limit the scope of the present invention in any way.

FIGURE LEGEND

FIGS. 1A-1C. The horizontal, white arrow represents the normal protein coding frame of a gene. FIG. 1A) a CRISPR/Cas system is used to introduce an indel at a position indicated by the arrow. In FIG. 1B), this indel has altered the protein coding frame, as indicated by the hatched section, leading to a null allele. In FIG. 1C), the CRISPR/Cas system is used to introduce two indels indicated by the arrows. In this instance the first indel again alters the protein coding frame while the second indel restores it. Consequently, all of the amino acids between the two indels are altered.

FIG. 2. The guide RNA (sgRNA) cassettes used are shown. The *Arabidopsis* U6 polIII promoter and terminator sequences are underlined. The 20 nt ALS2 specific sequences are shown in bold underlined type and the remainder of the sgRNA is in italics. The cassettes KG10177 (SEQ ID NO. 25), KG10190 (SEQ ID NO. 26) and KG10191 (SEQ ID NO. 27) express a single sgRNA. The cassette KG10240 (SEQ ID NO. 28) expresses all of the sgRNAs found in KG10177, KG10190 and KG10191 separated by tRNA sequences (bold italics).

FIGS. 3A-3C. FIG. 3A. guide RNA testing. The number of reads containing any indel (expressed as a percentage of the total number of sequence reads) was calculated for each of the four guide RNA constructs (sgRNA1=KG10177, sgRNA2=KG10190, sgRNA3=KG10191, sgRNA1+2+3=KG10240). FIG. 3B. The ALS2 target region is shown (WT, SEQ ID NO. 29) with the different PAM sequences underlined. For each guide RNA, examples of the indels produced are shown together with the percentage of reads containing that specific indel (SEQ ID NO. 30-49) FIG. 3C. The ALS1 target region is shown (WT, SEQ ID NO. 50) as well as the indels found at the ALS1 target region (SEQ ID NO. 51-66).

FIGS. 4A-4B. FIG. 4A. Both the DNA (SEQ ID NO. 20 and 21) and protein (SEQ ID NO. 22) sequences of the ALS1 and ALS2 regions targeted by the three guide RNAs are shown. The SNPs between the ALS1 and ALS2 genes are highlighted. The C to A SNP in ALS1 removes the sgRNA2 PAM sequence so that this guide RNA has no activity on ALS1. The ALS2 sequence on each sgRNA corresponds to either the Watson (+) or Crick (−) strand.

FIG. 4B. The sequences of the ALS genes from herbicide resistant plants. Deletions are indicated (−) and insertions are underlined. The consequence of the two indels on the amino acid sequence is shown in bold. The combination of guide RNAs that created the indel mutations (e.g. sgRNA2 & sgRNA1, 2+1) is shown. Figure discloses SEQ ID NOS 18-19, 3, 11, 3, 11, 4, 12, 4, 12, 3, 11, 3, 11, 3, 11, 4, 12, 17, 19, 5, and 13, respectively, in order of appearance.

EXAMPLES

Creating Novel Herbicide Resistance Through the Production of Indels
Constructs

The nucleotide sequences of the Cas9 ORF used is shown in SEQ ID NO 24. KG9387 (15758 bps) is a plant binary vector carrying this *S. pyogenes* Cas9 gene optimized for expression in *Arabidopsis*. This is linked to the *Arabidopsis* ubiquitin promoter (SEQ ID NO 23) for expression in plant cells (pUbi:Cas9). The vector carries the aad ORF which confers bacterial resistance to the antibiotic spectinomycin. The guide RNAs (sgRNAs) used in this study are shown in FIG. 2. Each guide RNA cassette, consisting of the *Arabidopsis* U6 promoter, the guide RNA and terminator sequence was synthesized and cloned into a plasmid vector.
DNA Preparation The vectors KG9387, KG10177, KG10190, KG10191, KG10240 were transformed to competent *E. coli* cells (TOP10 cells, Invitrogen) and the colonies were selected on LB medium containing the appropriate antibiotic(s). For large scale plasmid DNA isolation 50 ml cultures of each strain were made and plasmid DNA was isolated using standard protocols.
Tomato Protoplast Isolation and Transfection In vitro shoot cultures of *Solanum lycopersicon* var Moneyberg were maintained on MS20 medium with 0.8% agar in high plastic jars at 16/8 h photoperiod of 2000 lux at 25° C. and 60-70% RH. Young leaves (1 g) were gently sliced perpendicularly to the mid nerve to ease the penetration of the enzyme mixture. Sliced leaves were transferred to the enzyme mixture (2% Cellulase Onozuka RS, 0.4% Macerozyme Onozuka R10 in CPW9M) and cell wall digestion was allowed to proceed overnight in the dark at 25° C. The protoplasts were filtered through a 50 μm nylon sieve and were harvested by centrifugation for 5 minutes at 800 rpm. Protoplasts were resuspended in CPW9M (Frearson, 1973) medium and 3 mL CPW18S (Frearson et al., 1973, Developmental Biology, 33:130-137) was added at the bottom of each tube using a long-neck glass Pasteur pipette. Live protoplasts were harvested by centrifugation for 10 minutes at 800 rpm as the cell fraction at the interface between the sucrose and CPW9M medium. Protoplasts were counted and resuspended in MaMg (Negrutiu et al., 1987, Plant Molecular Biology, 8: 363-373) medium at a final density of $10^6$ per mL.

For the protoplast transfections 10 μg of KG9387 and 20 μg of one of the sgRNA expressing plasmids (KG10177, KG10190, KG10191, KG10240) mixed with 500 μL (500000 protoplasts) of the protoplast suspension and 500 μL of PEG solution (400 g/l poly(ethylene glycol) 4000, Sigma-Aldrich #81240; 0.1M $Ca(NO_3)_2$) was then added and the transfection was allowed to take place for 20 minutes at room temperature. Control samples were also produced by omitting one or both of the plasmids from the transfection. Then, 10 mL of 0.275 M $Ca(NO_3)_2$ solution was added and thoroughly, but gently mixed in. The protoplasts were harvested by centrifugation for 5 minutes at 800 rpm and resuspended in 9M culture medium at a density of $0.5 \times 10^6$ per ml and transferred to a 4 cm diameter petri dish and an equal volume of 2% alginate solution (20 g/l Alginate-Na (Sigma-Aldrich #A0682), 0.14 g/l $CaCl_2.2H_2O$, 90 g/l mannitol) was added. Then 1 ml aliquots of the protoplast and alginate mixture (125000 transfected protoplasts) were spread over Ca-Agar plates (72.5 g/l mannitol, 7.35 g/l $CaCl_2.2H_2O$, 8 g/l agar, pH5.8) and allowed to polymerize for 1 hour. The alginate disc containing the embedded protoplasts was then transferred to a 4 cm tissue culture dish containing 4 m of K8p (Kao, et al. 1975. Planta, 126: 105-110) culture medium. To determine the frequency of indel formation at the ALS1/ALS2 target sequence the disc of transfected protoplasts was removed from the dish after 48 hours, the alginate was dissolved, and the protoplasts were isolated by centrifugation. For the regeneration of calli, the protoplasts were incubated in the K8p medium for 21 days at 28° C. in the dark. After this period the discs of transfected protoplasts were transferred to solid GM medium (Tan et al., 1987, Plant Cell Reports, 6: 172-175) supplemented with 1 mg·$l^{-1}$ zeatin, 0.2 mg·$l^{-1}$ GA3 and 20 nM chlorsulfuron. The discs were transferred to fresh plates of the same GM medium every 3 weeks until the surviving calli were large enough to be picked with tweezers and were subsequently grown for genotyping on GM medium without chlorsulfuron.
Genotyping Protoplasts and Calli Total genomic DNA was isolated from tomato protoplasts (48 hrs post transfection) using the DNeasy Plant Mini Kit (Qiagen). This gDNA was then used in a PCR reaction to amplify either the ALS1 or ALS2 target site using the following primers (ALS1 Fw, 5'-TGGCGCTCAT-CACTTCTT (SEQ ID NO: 67); Rev, 5'-CGTTACCT-CAACAATAGGCGTTTCCT (SEQ ID NO: 68): ALS2 Fw, 5'-CACCTCATTTTCATGGCCCT (SEQ ID NO:69); Rev, 5'-AGCCTTCACGAACAACCCTA (SEQ ID NO:70)). These PCR products were used as templates to generate a library from each sample which were then pooled and sequenced using a 126 nt paired end Nano-run on the MiSeq platform (Illumina). Each sample was identified using a unique 5 bp tag. After sequencing the reads derived from each sample were processed to identify the number and types of sequence changes present at the target site. Herbicide resistant calli were genotyped directly using the direct PCR kit (Phire Plant Direct PCR kit, Thermo Scientific) and the gene specific primers described above. The ALS1 and ALS2 PCR products from the chlorsulfuron resistant calli were then Sanger sequenced to characterize the types of mutations at the target sites.

Plant Regeneration

Chlorsulfuron resistant calli were maintained on GM medium without the herbicide until the first shoots developed. The shooting calli were then placed on MS medium supplemented with 2 mg·l$^{-1}$ zeatin and 0.1 mg·l$^{-1}$ IAA media. After some time the regenerated tomato plantlets could be excised and rooted on MS medium supplemented with 0.5 mg·l$^{-1}$ IBA before transfer to the greenhouse.

Results

Targeted nucleases such as zinc finger nucleases (ZFN), TALENs, meganucleases and Crispr/Cas proteins can be targeted to a specific genomic sequence where they introduce mutations (indels). Indels are the consequence of DNA DSB induction by the targeted nuclease and the subsequent repair of this break by endogenous (error prone) DNA repair proteins. Induction of an indel in the coding sequence of a gene often leads to gene inactivation (creation of a null allele) due to the alteration of the coding frame. Indels that alter the coding frame introduce or delete either single base pairs or large stretches of sequence that are not divisible by three. As most indels fall into these categories, targeted nucleases are a very efficient tool for disrupting gene function in order to study their role in the cell. However, the disrupted reading frame can be restored to its original state by a second (closely linked) indel. For instance, if a single base pair insertion (+1) is introduced then a second downstream 1 bp deletion will restore the original reading frame. In this case all of the amino acids encoded between the two indels will be altered but the rest of the protein will remain unchanged. The number of altered amino acids is dependent on the distance between the two indels, but if this is relatively small then the protein is likely to retain the majority of its original function, but perhaps with some new beneficial properties due to the novel amino acids. This is a very powerful method to introduce allelic variation because a whole stretch of adjacent amino acids are altered which is more likely to result in phenotypic differences. In contrast, other more traditional forms of random mutagenesis such as treatment of tissues with a mutagen such as EMS, result in the alteration of individual single codons and consequently single amino acids throughout the protein. Not only can our method be used to alter several adjacent codons, it can also be targeted to a particular region or domain that is known to play a key role in the function of the protein.

The plant acetolactate synthase (ALS), also known as acetohydroxyacid synthase (AHAS) is the first enzyme in the biosynthesis of the branched chain amino acids isoleucine, valine and leucine. ALS is the target protein of the herbicide family known as ALS inhibitors. Several mutations in ALS, such as P197 (based on the *Arabidopsis* ALS protein, P184 is its equivalent in *S. lycopersicum*), are known to confer resistance to particular classes of ALS inhibitors. For instance dominant mutations at P197 are known to confer resistance to several sulfonylureas, such as chlorsulfuron (Roux et al. 2004. *Weed Res.* 45, 220-227). Herbicides such as chlorsulfuron can also be used as a selective agent in plant tissue culture. It can be added to plant synthetic medium and will prevent the growth of plant cells that lack mutations in ALS that confer ALS inhibitor tolerance. Our hypothesis was that the Crispr/Cas technology could be used to introduce indels flanking the P184 codon of ALS and that this would cause the protein reading frame between the indels to be altered. As the P184 codon would also be altered, such cells could be resistant to ALS inhibitor herbicides and thus can be selected for during tissue culture.

In tomato two copies of the ALS gene are present, ALS1 and ALS2, and an amino acid change at P184 in either gene can confer herbicide resistance. We designed 3 sgRNAs targeting the region around ALS2 P184 and linked these to the *Arabidopsis* U6 promoter for expression in plant cells giving the constructs KG10177, KG10190 & KG10191 (FIG. 2). The constructs KG10177 and KG10191 can in principle also produce mutations at ALS1 as the sequences of ALS1 and ALS2 are well conserved. However, the sgRNA of KG10190 cannot because ALS1 lacks the PAM sequence necessary for this guide RNA. In order to express all three guide RNAs simultaneously in the plant cell we also generated a construct with each of the sgRNAs separated by a tRNA sequence (KG10240) as has been previously reported (Xie el al. 2015. *Proc. Natl. Acad. Sci USA* 112, 3570-3575). When this array of the three sgRNAs are expressed in the cell the intervening tRNA sequences are removed by the endogenous tRNA processing machinery, releasing the individual sgRNAs that are then able to generate indels. First we tested whether these sgRNAs were active in tomato. We isolated protoplasts from tomato leaves and then introduced two constructs into these cells, KG9387 expressing the Cas9 protein together with one of the plasmids expressing the guide RNAs. After 48 hours the genomic DNA was isolated from the protoplasts and both the ALS1 and ALS2 target sites were amplified from each sample. These amplicons were then used as a template for the construction of a library that was then sequenced on the MiSeq platform. The percentage of reads containing a specific indel mutation was calculated, allowing us to determine the efficiency of each guide RNA. The results are shown in FIGS. 3A-3C. Transfection of the Cas9 expressing construct alone, KG9387, did not result in sequence reads with indels. However, when KG9387 was transfected together with one of the guide RNA expressing plasmids we did recover reads with indels. We found that all of the guide RNAs were active in tomato protoplasts and that the construct KG10240, expressing all three guide RNAs, resulted in reads that contained more than one indel. We then repeated the experiment and then grew the protoplasts on medium containing the ALS inhibitor chlorsulfuron. The results are shown in Table 2.

TABLE 2

Number of chlorsulfuron resistant calli recovered after the transfection of tomato protoplasts.

| Plasmids transfected to protoplasts | Number of chlorsulfuron resistant calli |
| --- | --- |
| KG9387 | 0 |
| KG9387 + KG10177 | 0 |
| KG9387 + KG10190 | 0 |
| KG9387 + KG10191 | 0 |
| KG9387 + KG10240 | 23 |

When only the Cas9 expression plasmid KG9387 was transfected, or KG9387 in combination with the plasmids that express a single guide RNA, no chlorsulfuron resistant calli were recovered. This demonstrates that the introduction of a single indel mutation does not result in a chlorsulfuron resistant phenotype. However, when KG9387 was transfected together with KG10240 that expresses all three guide RNAs then we were able to recover chlorsulfuron resistant calli. We amplified the ALS1 and ALS2 target sites from each resistant callus and sequenced these to determine the indel mutations present. The results are shown in FIGS. 4A-4B. We found that all of the call contained two linked indel mutations in either ALS1 or ALS2. Surprisingly, the indel mutations that gave chlorsulfuron resistance were identical in multiple calli and were always biallelic (both alleles of ALS1 or ALS2 containing the same two indels). As a callus is derived from a single protoplast, we can assume these were derived from independent mutagenesis events. The calli also contained additional mutations in the other gene. For instance, calli with two indels in ALS2 often had a single indel mutation in ALS1. The single mutation was variable and often led to the disruption of gene function, providing further evidence that the resistant calli were independent events.

When we studied the ALS1 or ALS2 genes containing two indels in detail, we found that the first indel (either the loss or gain of a single nucleotide) altered the protein reading frame while the second indel, also a single nucleotide change, restored it. Such indels can be described a −1/+1 or +1/−1. Consequently, the length of the coding sequence was unaltered. Interestingly, we did not find any other sizes of indels, for instance −2/+2, −1/+4, that would also restore the reading frame. In all of the sequenced calli the protein reading frame between the two indels (including the codon P184) was changed, leading to the presence of 2-5 novel adjacent amino acids in the ALS protein.

In FIGS. 3B and 3C we show that the expression of the three guide RNAs simultaneously in protoplasts leads results in the induction of two indels flanking the P184 codon. Several of these contained two indel mutations that resulted in the restoration of the reading frame. However, when herbicide selection was applied we only recovered calli with pairs of indels at specific positions and of specific size. For instance, for ALS2 we only recovered two different alleles (GQCRGGLIGT (SEQ ID NO:71) & GQSARRMIGT (SEQ ID NO:72)), suggesting that only these changes lead to a chlorsulfuron resistant phenotype. Therefore we conclude that other pairs of indel mutations present in the sequence data that result in other amino acid changes (e.g. GQVPG-GLMIGT (SEQ ID NO:73) and GRRGGLIGT (SEQ ID NO:74)) but were not recovered in the chlorsulfuron resistant calli, were therefore not resistance alleles. We also found similar pairs of indel mutations (−1/+1) flanking the P184 codon of in some chlorsulfuron resistant call, although these indels gave a somewhat different protein sequence (GQVQGGLIGT (SEQ ID NO:75)). Under chlorsulfuron selection pressure the wild type ALS proteins are inhibited by the herbicide, leaving only the chlorsulfuron resistant alleles available for branched amino acid synthesis. Therefore, the alteration of multiple adjacent amino acids (up to 5) still results in a functional ALS protein that retains its original function in the branched amino acid synthesis pathway.

The chlorsulfuron resistant alleles that we have identified have, to our knowledge, never previously been described. Therefore, they represent novel alleles that could be introduced in the same way into the endogenous ALS genes of other plant species. These calli were selected using the sulfonylurea chlorsulfuron, but a wide range of other ALS inhibitors is known. The degree to which a specific ALS mutation (e.g. P184S) confers resistance depends upon the specific ALS inhibitor used and the concentration used. The most useful ALS mutations deliver resistance to all of the available ALS inhibitors at high concentrations. It is possible that the resistance alleles that we describe here give resistance to a wider range of ALS inhibitors and/or at high concentrations, particularly since multiple amino acids have been altered.

We have shown that the introduction of two indels in a coding sequence can be used to introduce allelic variation, leading to the production of a protein with novel properties. This method is applicable to any cell type and should find applications in all aspects of biotechnology.

The invention claimed is:

1. A method for producing a protein having a gain-of-function by targeted alteration of a coding sequence (CDS) in between target sites wherein nontargeted CDS is unaltered in duplex DNA in a cell, comprising
exposing the duplex DNA to at least two site-specific nucleases, wherein a first site-specific nuclease targets the DNA at a first position within the CDS and cleaves the DNA generating a first indel at a first location within the CDS, and wherein a second site-specific nuclease targets the DNA at a second position within the CDS and cleaves the DNA generating a second indel at a second location within the same CDS, wherein the first and second indel are frame shift mutations, resulting in an altered part of the CDS, wherein the altered part of the CDS has a length between 2-15 codons, wherein the CDS before the first indel and after the second indel remain in the same reading frame, wherein the altered part of the CDS starts with the first indel up to and including the second indel, wherein the altered part of the CDS does not comprise a stop codon; and
selecting a cell comprising the targeted alteration,
wherein the CDS comprising the targeted alteration encodes the protein having a gain of function, and
wherein the protein having a gain-of-function is produced with a higher efficiency than with an identical method using a single site-specific nuclease.

2. The method according to claim 1, wherein the CDS is altered by introducing or deleting at least one nucleotide at the first location and by introducing or deleting at least one nucleotide at the second location, wherein the total of introduced nucleotides preferably is 0, 3, 6, 9 or 12 and/or wherein the total of deleted nucleotides preferably is 0, 3, 6, 9 or 12.

3. The method according to claim 1, wherein the altered part of the CDS has a length between 2-10 or 2-5 codons.

4. The method according to claim 1, wherein the altered part of the CDS has a length of 2, 3, 4, 5, 6, 7, 8, 9 or 10 codons.

5. The method according to claim 1, wherein at least one of the nucleases is a CRISPR nuclease and wherein the method further comprises exposing the duplex DNA to:
  (i) a first guide RNA that comprises a first guide sequence for targeting the first nuclease to the first location in the duplex DNA; and/or
  (ii) a second guide RNA that comprises a second guide sequence for targeting the second nuclease to the second location in the duplex DNA.

6. The method according to claim 5, wherein the at least one CRISPR nuclease is Cas9 or Cpf1.

7. The method according to claim 1, wherein at least one of the nucleases is selected from the group consisting of a zinc finger nuclease, a meganuclease and a TALEN.

8. The method according to claim 1, wherein the duplex DNA is exposed to two, three or four site-specific nucleases and wherein the two, three or four site-specific nucleases cleave the duplex DNA of the same CDS.

9. The method according to claim 1, wherein at least one of the site-specific nucleases and/or one or more guide RNAs is introduced into the cell.

10. The method according to claim 1, wherein the cell is transfected with a nucleic acid construct encoding at least one of the site-specific nucleases and/or one or more guide RNAs.

11. The method according to claim 10, wherein the nucleic acid construct encodes at least two guide RNAs.

12. The method according to claim 1, further comprising regenerating a plant or descendent thereof comprising the altered part of the CDS.

* * * * *

SEQUENCE LISTING

```
<160> NUMBER OF SEQ ID NOS: 75

<210> SEQ ID NO 1
<211> LENGTH: 1980
<212> TYPE: DNA
<213> ORGANISM: Solanum lycopersicon

<400> SEQUENCE: 1
atggcggctg ctgcctcacc atctccatgt ttctccaaaa ccctacctcc atcttcctcc      60
aaatcttcca ccattctacc tagatctacc ttctctttcc acaatcaccc acaaaaagcc     120
tcaccccttc atctcatcca cgctcaacat aatcgtcgtg gttttgccgt tgccaatgtc     180
gtcatatcca ctaccaccca taacgacgtt tctgaacctg aaacattcgt ttcccgtttc     240
gcccctgacg aacccagaaa gggttgtgat gttcttgtgg aggcacttga aagggaaggt     300
gttacggatg tatttgcata cccaggaggt gcttctatgg agattcatca agctttgaca     360
cgttcgaata ttattcgtaa tgtgctacca cgtcatgagc aaggtggtgt gtttgctgca     420
gagggttacg cacgggctac tgggttccct ggtgtttgca ttgctacctc tggtcccgga     480
gctacaaatc ttgttagtgg tcttgcggat gctttgttag atagtattcc gattgttgct     540
attacaggtc aagtgccaag gaggatgatt ggtactgatg cgttccagga aacgcctatt     600
gttgaggtaa cgagatctat tacgaagcat aattatcttg ttatggatgt agaagatatt     660
```

```
cctagggttg ttcgtgaagc attttttctt gcgaaatcgg gacggcctgg cccagttttg      720
attgatgtac ctaaggatat tcagcaacaa ttggtgatac ctaattggga tcagccaatg      780
aggttgcctg gttacatgtc taggttacct aaattgccta atgaaatgct tttggaacaa      840
attgttaggc tgatttccga gtcgaagaag cctgttttgt atgtgggtgg tgggtgttcg      900
caatcaagtg aggagctgag acgatttgtg gagcttacag gtattcctgt agcgagtact      960
ttgatgggtc ttggagcttt tccaactggg atgagctttc acttcaaat gttgggtatg     1020 catggaactg tgtatgctaa ttatgctgtg gatagtagtg atttgttgct tgcatttggg     1080
gtgaggtttg atgatcgagt tactggtaaa ttggaagctt ttgctagtcg agcgaaaatt     1140
gtccacattg atattgattc ggcagagatt ggaaaaaaca agcaacctca tgtttccatt     1200
tgtgcagata tcaagttggc attacagggt ttgaattcca tattggaggg taaagaaggt     1260
aagatgaagt tagattttc tgcctggagg caggagttaa cggagcagaa gatgaagtac     1320
ccactgaatt ttaagacttt tggtgatgcc atccctccac aatatgctat tcaggttctt     1380
gatgagttaa ctaacggaaa tgccattatt agtactggtg tggggcaaca ccagatgtgg     1440
gctgcccaat actataagta caaaaagcca cgccaatggt tgacatctgg tggattagga     1500
gcaatgggat ttggtttgcc tgctgctata ggtgcggctg ttgggagacc gggtgagatt     1560
gtggttgaca ttgacggtga tgggagtttt atcatgaatg tgcaagagtt agcaacaatt     1620
aaggtggaga atctcccagt taagattatg ttgctgaata atcaacactt gggaatggtg     1680
gttcaatggg aggatcgatt ctataaagct aacagagcac acacttactt gggtgaccct     1740
tctaacgagg aagagatctt ccctaatatg ttgaaatttg cagaggcttg tggcgtacct     1800
gctgcaagag tgtcacacag ggatgatctt agagctgcca ttcaaaagat gttagacact     1860
cctgggccat acttgttgga tgtgattgta cctcatcagg agcacgttct acctatgatt     1920
cccagcggtg gtgctttcaa agatgtgatc acggagggcg atgggagatg ttcctattga     1980
```

<210> SEQ ID NO 2
<211> LENGTH: 1974
<212> TYPE: DNA
<213> ORGANISM: Solanum lycopersicon

<400> SEQUENCE: 2

```
atggcggctg catctccatc tccttgtttt tccaaaaccc tacctccatc ttcatcaaaa       60
tcttccaccc ttcttcccaa atctaccttt actttccaca atcaccctaa aaaagcatca      120
ccccttcacc ttacacacac ccaacatcat agccgtttca ctgtttcaaa tgtcatccta      180
tcaaccacga cgcatgacga cgtttctgaa cccgaaatct tgtttcccg tttcgcccct      240 gacgaaccca gaaaggggttg tgatgttctt gtggaggcac ttgaaaggga aggggttaag      300
gatgtgtttg catacccagg aggtgcttcc atggagattc atcaggcttt gacacgttca      360
aatattattc gtaatgtgct gccacgtcat gaacagggtg gtgtgtttgc tgcagagggt      420
tacgcacggg ctactgggtt ccctggtgtt tgtattgcta catctggtcc gggagctacg      480
aatcttgtta gcggtcttgc tgatgctttg ttggatagta tcccgattgt tgctattacc      540
ggtcaagtgc cgaggaggat gattggtact gatgcgtttg aggaaactcc tattgttgag      600
gtaacgagat ccattacgaa gcataattat cttgttatgg atgtagagga tattcctagg      660
gttgttcgtg aagcgttttt tctagcgaaa tcaggacggc ctggacctgt tttgattgat      720
gttcctaagg atattcagca acaattggtg atacctaatt gggatcagcc aatgaggttg      780
```

```
cctggttaca tgtctaggtt gcctaaatta cctaatgaga tgcttttgga acaaattgtt      840
aggctgattt cagagtcaaa gaagcctgtt ttgtatgtgg ggggtgggtg ttcacagtcg      900
agtgaggagc tgagacgctt tgtggagctt acgggtattc ctgtggcgag tactttgatg      960
ggtcttggag cttttccaag tggggatgag ctttctcttc aaatgttggg tatgcatggg     1020
actgtgtatg ctaattatgc ggtggatagt agtgatttgt tgcttgcatt tggggtgagg     1080
tttgatgatc gagttactgg taaattggaa gcttttgcta gccgagctaa gattgtccat     1140
attgatattg attcggctga gattggaaag aacaagcaac tcatgtttc catctgtgca      1200 gatatcaagt tggcattaca gggtttgaat tccatattcg agagtaaaaa aggtaagctg     1260
aagttggact tttctgcttg gaggcaggag ttaacggagc agaaggtgaa gtacccattg     1320 aatttttaaga ctttcggtga agccatccct ccccaatatg ctattcaggt tcttgatgag     1380
ttaactaacg gaaatgccat cattagtact ggtgtggggc aacaccaaat gtgggctgcc     1440
caacactaca agtacaaaaa gccacgccaa tggcttacat ctggtggatt aggagcaatg     1500
ggatttggtt tgcctgctgc tataggtgcg gctgttggaa gaccggggtga gattgtggtt     1560 gatattgatg gtgatgggag ttttatcatg aatgtgcagg agttggcaac aattaaggtg     1620
gagaatctcc cagttaagat tatgttgctg aataatcaac acttgggaat ggtggttcag     1680
tgggaggatc gattctataa ggctaacaga gcacacactt acttgggtaa tcctgctaat     1740
gaggaagaga tcttccctaa tatgctgaaa tttgcagagg cttgtggcgt acctgctgca     1800
agagtgtcac acagggatga tcttagagct gccattcaaa agatgttaga cactcctggg     1860
ccatacttgt tggatgtgat tgtacctcat caggagcatg ttctaccgat gattcccagt     1920
ggcggtgctt tcaaagatgt gattacggag ggtgatggga gacgttccta ttga          1974
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C22

<400> SEQUENCE: 3
ggtcagtgcc gaggaggatt gatt                                              24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C17

<400> SEQUENCE: 4
ggtcaaagtg ccaggaggat gatt                                              24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: C14

<400> SEQUENCE: 5
ggtcaagtgc aaggaggatt gatt                                          24

<210> SEQ ID NO 6
<211> LENGTH: 1974
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: ALS2_C22

<400> SEQUENCE: 6

| | | |
|---|---|---|
| atggcggctg catctccatc tccttgtttt tccaaaaccc tacctccatc ttcatcaaaa | 60 |
| tcttccaccc ttcttcccaa atctacccttt actttccaca atcaccctaa aaaagcatca | 120 |
| cccctttcacc ttacacacac ccaacatcat agccgtttca ctgtttcaaa tgtcatccta | 180 |
| tcaaccacga cgcatgacga cgtttctgaa cccgaaatct ttgtttcccg tttcgcccct | 240 |
| gacgaaccca gaaaggggttg tgatgttctt gtggaggcac ttgaaaggga gggggttaag | 300 |
| gatgtgtttg catacccagg aggtgcttcc atggagattc atcaggcttt gacacgttca | 360 |
| aatattattc gtaatgtgct gccacgtcat gaacagggtg gtgtgtttgc tgcagagggt | 420 |
| tacgcacggg ctactgggtt ccctggtgtt tgtattgcta catctggtcc gggagctacg | 480 |
| aatcttgtta gcggtcttgc tgatgctttg ttggatagta tcccgattgt tgctattacc | 540 |
| ggtcagtgcc gaggaggatt gattggtact gatgcgtttc aggaaactcc tattgttgag | 600 |
| gtaacgagat ccattacgaa gcataattat cttgttatgg atgtagagga tattcctagg | 660 |
| gttgttcgtg aagcgttttt tctagcgaaa tcaggacggc ctggacctgt tttgattgat | 720 |
| gttcctaagg atattcagca acaattggtg atacctaatt gggatcagcc aatgaggttg | 780 |
| cctggttaca tgtctaggtt gcctaaatta cctaatgaga tgcttttgga acaaattgtt | 840 |
| aggctgattt cagagtcaaa gaagcctgtt ttgtatgtgg ggggtgggtg ttcacagtcg | 900 |
| agtgaggagc tgagacgctt tgtggagctt acgggtattc ctgtggcgag tactttgatg | 960 |
| ggtcttggag cttttccaag tggggatgag cttttctcttc aaatgttggg tatgcatggg | 1020 |
| actgtgtatc taattatgc ggtggatagt agtgatttgt tgcttgcatt ggggtgagg | 1080 |
| tttgatgatc gagttactgg taaattggaa gcttttgcta gccgagctaa gattgtccat | 1140 |
| attgatattg attcggctga gattggaaag aacaagcaac tcatgtttc catctgtgca | 1200 |
| gatatcaagt tggcattaca gggtttgaat tccatattcg agagtaaaaa aggtaagctg | 1260 |
| aagttggact ttctgcttg gaggcaggag ttaacggagc agaaggtgaa gtacccattg | 1320 |
| aattttaaga ctttcggtga agccatccct ccccaatatg ctattcaggt tcttgatgag | 1380 |
| ttaactaacg gaaatgccat cattagtact ggtgtgggggc aacaccaaat gtgggctgcc | 1440 |
| caacactaca agtacaaaaa gccacgccaa tggcttacat ctggtggatt aggagcaatg | 1500 |
| ggatttggtt tgcctgctgc tataggtgcg gctgttggaa gaccgggtga gattgtggtt | 1560 |
| gatattgatg gtgatgggag ttttatcatg aatgtgcagg agttggcaac aattaaggtg | 1620 |
| gagaatctcc cagttaagat tatgttgctg aataatcaac acttgggaat ggtggttcag | 1680 |
| tgggaggatc gattctataa ggctaacaga gcacacactt acttgggtaa tcctgctaat | 1740 |
| gaggaagaga tcttccctaa tatgctgaaa tttgcagagg cttgtggcgt acctgctgca | 1800 |

| | |
|---|---|
| agagtgtcac acagggatga tcttagagct gccattcaaa agatgttaga cactcctggg | 1860 |
| ccatacttgt tggatgtgat tgtacctcat caggagcatg ttctaccgat gattcccagt | 1920 |
| ggcggtgctt tcaaagatgt gattacggag ggtgatggga gacgttccta ttga | 1974 |

<210> SEQ ID NO 7
<211> LENGTH: 1974
<212> TYPE: DNA
<213> ORGANISM: Artificial Sequence
<220> FEATURE:
<223> OTHER INFORMATION: Description of Artificial Sequence: Synthetic
  polynucleotide
<220> FEATURE:
<223> OTHER INFORMATION: ALS2_C17

<400> SEQUENCE: 7

| | |
|---|---|
| atggcggctg catctccatc tccttgtttt tccaaaaccc tacctccatc ttcatcaaaa | 60 |
| tcttccaccc ttcttcccaa atctaccttt actttccaca atcaccctaa aaaagcatca | 120 |
| ccccttcacc ttacacacac ccaacatcat agccgtttca ctgtttcaaa tgtcatccta | 180 |
| tcaaccacga cgcatgacga cgtttctgaa cccgaaatct ttgtttcccg tttcgcccct | 240 |
| gacgaaccca gaaagggttg tgatgttctt gtggaggcac ttgaaaggga agggggttaag | 300 |
| gatgtgtttg cataccccagg aggtgcttcc atggagattc atcaggcttt gacacgttca | 360 |
| aatattattc gtaatgtgct gccacgtcat gaacagggtg gtgtgtttgc tgcagagggt | 420 |
| tacgcacggg ctactgggtt ccctggtgtt tgtattgcta catctggtcc gggagctacg | 480 |
| aatcttgtta gcggtcttgc tgatgctttg ttggatagta tcccgattgt tgctattacc | 540 |
| ggtcaaagtg ccaggaggat gattggtact gatgcgtttc aggaaactcc tattgttgag | 600 |
| gtaacgagat ccattacgaa gcataattat cttgttatgg atgtagagga tattcctagg | 660 |
| gttgttcgtg aagcgttttt tctagcgaaa tcaggacggc ctggacctgt tttgattgat | 720 |
| gttcctaagg atattcagca acaattggtg atacctaatt gggatcagcc aatgaggttg | 780 |
| cctggttaca tgtctaggtt gcctaaatta cctaatgaga tgcttttgga acaaattgtt | 840 |
| aggctgattt cagagtcaaa gaagcctgtt ttgtatgtgg ggggtgggtg ttcacagtcg | 900 |
| agtgaggagc tgagacgctt tgtggagctt acgggtattc ctgtggcgag tactttgatg | 960 |
| ggtcttggag cttttccaag tggggatgag cttctcttc aaatgttggg tatgcatggg | 1020 |
| actgtgtatc taattatgc ggtggatagt agtgatttgt tgcttgcatt tggggtgagg | 1080 |
| tttgatgatc gagttactgg taaattggaa gcttttgcta gccgagctaa gattgtccat | 1140 |
| attgatattg attcggctga gattggaaag aacaagcaac tcatgttttc catctgtgca | 1200 |
| gatatcaagt tggcattaca gggtttgaat tccatattcg agagtaaaaa aggtaagctg | 1260 |
| aagttggact ttctgcttg gaggcaggag ttaacggagc agaaggtgaa gtacccattg | 1320 |
| aattttaaga ctttcggtga agccatccct ccccaatatg ctattcaggt tcttgatgag | 1380 |
| ttaactaacg gaaatgccat cattagtact ggtgtgggc aacaccaaat gtgggctgcc | 1440 |
| caacactaca agtacaaaaa gccacgccaa tggcttacat ctggtggatt aggagcaatg | 1500 |
| ggatttggtt tgcctgctgc tataggtgcg gctgttggaa gaccgggtga gattgtggtt | 1560 |
| gatattgatg tgatgggag tttatcatg aatgtgcagg agttggcaac aattaaggtg | 1620 |
| gagaatctcc cagttaagat tatgttgctg aataatcaac acttgggaat ggtggttcag | 1680 |
| tgggaggatc gattctataa ggctaacaga gcacacactt acttgggtaa tcctgctaat | 1740 |
| gaggaagaga tcttccctaa tatgctgaaa tttgcagagg cttgtggcgt acctgctgca | 1800 |

-continued

```
agagtgtcac acagggatga tcttagagct gccattcaaa agatgttaga cactcctggg      1860
ccatacttgt tggatgtgat tgtacctcat caggagcatg ttctaccgat gattcccagt      1920
ggcggtgctt tcaaagatgt gattacggag ggtgatggga cacgttccta ttga            1974
```

<210> SEQ ID NO 8
<211> LENGTH: 1980
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: ALS1_C14

<400> SEQUENCE: 8

```
atggcggctg ctgcctcacc atctccatgt ttctccaaaa ccctacctcc atcttcctcc        60
aaatcttcca ccattctacc tagatctacc ttctctttcc acaatcaccc acaaaaagcc       120
tcaccccttc atctcatcca cgctcaacat aatcgtcgtg gttttgccgt tgccaatgtc       180
gtcatatcca ctaccaccca taacgacgtt tctgaacctg aaacattcgt ttcccgtttc       240
gcccctgacg aacccagaaa gggttgtgat gttcttgtgg aggcacttga aagggaaggt       300
gttacggatg tatttgcata cccaggaggt gcttctatgg agattcatca agctttgaca       360
cgttcgaata ttattcgtaa tgtgctacca cgtcatgagc aagtggtgtg tttgctgca       420 gagggttacg cacgggctac tggggttccct ggtgtttgca ttgctacctc tggtcccgga      480
gctacaaatc ttgttagtgg tcttgcggat gctttgttag atagtattcc gattgttgct       540
attacaggtc aagtgcaagg aggattgatt ggtactgatg cgttccagga aacgccatt       600 gttgaggtaa cgagatctat tacgaagcat aattatcttg ttatggatgt agaagatatt       660
cctagggttg ttcgtgaagc attttttctt gcgaaatcgg gacggcctgg cccagttttg      720
attgatgtac ctaaggatat tcagcaacaa ttggtgatac ctaattggga tcagccaatg      780
aggttgcctg gttacatgtc taggttacct aaattgccta atgaaatgct tttggaacaa      840
attgttaggc tgatttccga gtcgaagaag cctgttttgt atgtgggtgg tgggtgttcg      900
caatcaagtg aggagctgag acgatttgtg agcttacag gtattcctgt agcgagtact       960
ttgatgggtc ttggagcttt tccaactggg gatgagcttt cacttcaaat gttgggtatg      1020 catgaactg tgtatgctaa ttatgctgtg atagtagtga atttgttgct tgcatttggg      1080
gtgaggtttg atgatcgagt tactggtaaa ttggaagctt tgctagtcg agcgaaaatt      1140 gtccacattg atattgattc ggcagagatt ggaaaaaaca gcaacctca tgtttccatt      1200 tgtgcagata tcaagttggc attacagggt ttgaattcca tattggaggg taaagaaggt      1260
aagatgaagt tagattttc tgcctggagg caggagttaa cggagcagaa gatgaagtac      1320
ccactgaatt ttaagacttt tggtgatgcc atccctccac aatatgctat tcaggttctt      1380
gatgagttaa ctaacggaaa tgccattatt agtactggtg tggggcaaca ccagatgtgg      1440
gctgcccaat actataagta caaaaagcca cgccaatggt tgacatctgg tggattagga      1500
gcaatgggat ttggttttgcc tgctgctata ggtgcggctg ttgggagacc gggtgagatt      1560
gtggttgaca ttgacggtga tgggagtttt atcatgaatg tgcaagagtt agcaacaatt      1620
aaggtggaga atctcccagt taagattatg ttgctgaata tcaacacttt gggaatggtg      1680
gttcaatggg aggatcgatt ctataaagct aacagagcac acacttactt gggtgaccct      1740
tctaacgagg aagagatctt ccctaatatg ttgaaatttg cagaggcttg tggcgtacct      1800
```

-continued

```
gctgcaagag tgtcacacag ggatgatctt agagctgcca ttcaaaagat gttagacact    1860
cctgggccat acttgttgga tgtgattgta cctcatcagg agcacgttct acctatgatt    1920
cccagcggtg gtgctttcaa agatgtgatc acggagggcg atgggagatg ttcctattga    1980
```

<210> SEQ ID NO 9
<211> LENGTH: 659
<212> TYPE: PRT
<213> ORGANISM: Solanum lycopersicon

<400> SEQUENCE: 9

```
Met Ala Ala Ala Ser Pro Ser Pro Cys Phe Ser Lys Thr Leu Pro
1               5                   10                  15

Pro Ser Ser Ser Lys Ser Ser Thr Ile Leu Pro Arg Ser Thr Phe Ser
            20                  25                  30

Phe His Asn His Pro Gln Lys Ala Ser Pro Leu His Leu Ile His Ala
        35                  40                  45

Gln His Asn Arg Arg Gly Phe Ala Val Ala Asn Val Val Ile Ser Thr
    50                  55                  60

Thr Thr His Asn Asp Val Ser Glu Pro Glu Thr Phe Val Ser Arg Phe
65                  70                  75                  80

Ala Pro Asp Glu Pro Arg Lys Gly Cys Asp Val Leu Val Glu Ala Leu
                85                  90                  95

Glu Arg Glu Gly Val Thr Asp Val Phe Ala Tyr Pro Gly Gly Ala Ser
            100                 105                 110

Met Glu Ile His Gln Ala Leu Thr Arg Ser Asn Ile Ile Arg Asn Val
        115                 120                 125

Leu Pro Arg His Glu Gln Gly Gly Val Phe Ala Ala Glu Gly Tyr Ala
    130                 135                 140

Arg Ala Thr Gly Phe Pro Gly Val Cys Ile Ala Thr Ser Gly Pro Gly
145                 150                 155                 160

Ala Thr Asn Leu Val Ser Gly Leu Ala Asp Ala Leu Leu Asp Ser Ile
                165                 170                 175

Pro Ile Val Ala Ile Thr Gly Gln Val Pro Arg Arg Met Ile Gly Thr
            180                 185                 190

Asp Ala Phe Gln Glu Thr Pro Ile Val Glu Val Thr Arg Ser Ile Thr
        195                 200                 205

Lys His Asn Tyr Leu Val Met Asp Val Glu Asp Ile Pro Arg Val Val
    210                 215                 220

Arg Glu Ala Phe Phe Leu Ala Lys Ser Gly Arg Pro Gly Pro Val Leu
225                 230                 235                 240

Ile Asp Val Pro Lys Asp Ile Gln Gln Gln Leu Val Ile Pro Asn Trp
                245                 250                 255

Asp Gln Pro Met Arg Leu Pro Gly Tyr Met Ser Arg Leu Pro Lys Leu
            260                 265                 270

Pro Asn Glu Met Leu Leu Glu Gln Ile Val Arg Leu Ile Ser Glu Ser
        275                 280                 285

Lys Lys Pro Val Leu Tyr Val Gly Gly Gly Cys Ser Gln Ser Ser Glu
    290                 295                 300

Glu Leu Arg Arg Phe Val Glu Leu Thr Gly Ile Pro Val Ala Ser Thr
305                 310                 315                 320

Leu Met Gly Leu Gly Ala Phe Pro Thr Gly Asp Glu Leu Ser Leu Gln
                325                 330                 335

Met Leu Gly Met His Gly Thr Val Tyr Ala Asn Tyr Ala Val Asp Ser
            340                 345                 350
```

```
Ser Asp Leu Leu Leu Ala Phe Gly Val Arg Phe Asp Arg Val Thr
        355                 360                 365

Gly Lys Leu Glu Ala Phe Ala Ser Arg Ala Lys Ile Val His Ile Asp
    370                 375                 380

Ile Asp Ser Ala Glu Ile Gly Lys Asn Lys Gln Pro His Val Ser Ile
385                 390                 395                 400

Cys Ala Asp Ile Lys Leu Ala Leu Gln Gly Leu Asn Ser Ile Leu Glu
                405                 410                 415

Gly Lys Glu Gly Lys Met Lys Leu Asp Phe Ser Ala Trp Arg Gln Glu
                420                 425                 430

Leu Thr Glu Gln Lys Met Lys Tyr Pro Leu Asn Phe Lys Thr Phe Gly
        435                 440                 445

Asp Ala Ile Pro Pro Gln Tyr Ala Ile Gln Val Leu Asp Glu Leu Thr
        450                 455                 460

Asn Gly Asn Ala Ile Ile Ser Thr Gly Val Gly Gln His Gln Met Trp
465                 470                 475                 480

Ala Ala Gln Tyr Tyr Lys Tyr Lys Lys Pro Arg Gln Trp Leu Thr Ser
                485                 490                 495

Gly Gly Leu Gly Ala Met Gly Phe Gly Leu Pro Ala Ala Ile Gly Ala
                500                 505                 510

Ala Val Gly Arg Pro Gly Glu Ile Val Val Asp Ile Asp Gly Asp Gly
        515                 520                 525

Ser Phe Ile Met Asn Val Gln Glu Leu Ala Thr Ile Lys Val Glu Asn
530                 535                 540

Leu Pro Val Lys Ile Met Leu Leu Asn Asn Gln His Leu Gly Met Val
545                 550                 555                 560

Val Gln Trp Glu Asp Arg Phe Tyr Lys Ala Asn Arg Ala His Thr Tyr
                565                 570                 575

Leu Gly Asp Pro Ser Asn Glu Glu Ile Phe Pro Asn Met Leu Lys
                580                 585                 590

Phe Ala Glu Ala Cys Gly Val Pro Ala Ala Arg Val Ser His Arg Asp
        595                 600                 605

Asp Leu Arg Ala Ala Ile Gln Lys Met Leu Asp Thr Pro Gly Pro Tyr
        610                 615                 620

Leu Leu Asp Val Ile Val Pro His Gln Glu His Val Leu Pro Met Ile
625                 630                 635                 640

Pro Ser Gly Gly Ala Phe Lys Asp Val Ile Thr Glu Gly Asp Gly Arg
                645                 650                 655

Cys Ser Tyr

<210> SEQ ID NO 10
<211> LENGTH: 657
<212> TYPE: PRT
<213> ORGANISM: Solanum lycopersicon

<400> SEQUENCE: 10

Met Ala Ala Ala Ser Pro Ser Pro Cys Phe Ser Lys Thr Leu Pro Pro
1               5                   10                  15

Ser Ser Ser Lys Ser Ser Thr Leu Leu Pro Lys Ser Thr Phe Thr Phe
            20                  25                  30

His Asn His Pro Lys Lys Ala Ser Pro Leu His Leu Thr His Thr Gln
        35                  40                  45

His His Ser Arg Phe Thr Val Ser Asn Val Ile Leu Ser Thr Thr Thr
    50                  55                  60
```

```
His Asp Asp Val Ser Glu Pro Glu Ile Phe Val Ser Arg Phe Ala Pro
 65                  70                  75                  80

Asp Glu Pro Arg Lys Gly Cys Asp Val Leu Val Glu Ala Leu Glu Arg
                 85                  90                  95

Glu Gly Val Lys Asp Val Phe Ala Tyr Pro Gly Gly Ala Ser Met Glu
            100                 105                 110

Ile His Gln Ala Leu Thr Arg Ser Asn Ile Ile Arg Asn Val Leu Pro
        115                 120                 125

Arg His Glu Gln Gly Gly Val Phe Ala Ala Glu Gly Tyr Ala Arg Ala
130                 135                 140

Thr Gly Phe Pro Gly Val Cys Ile Ala Thr Ser Gly Pro Gly Ala Thr
145                 150                 155                 160

Asn Leu Val Ser Gly Leu Ala Asp Ala Leu Leu Asp Ser Ile Pro Ile
                165                 170                 175

Val Ala Ile Thr Gly Gln Val Pro Arg Arg Met Ile Gly Thr Asp Ala
            180                 185                 190

Phe Gln Glu Thr Pro Ile Val Glu Val Thr Arg Ser Ile Thr Lys His
        195                 200                 205

Asn Tyr Leu Val Met Asp Val Glu Asp Ile Pro Arg Val Val Arg Glu
210                 215                 220

Ala Phe Phe Leu Ala Lys Ser Gly Arg Pro Gly Pro Val Leu Ile Asp
225                 230                 235                 240

Val Pro Lys Asp Ile Gln Gln Gln Leu Val Ile Pro Asn Trp Asp Gln
                245                 250                 255

Pro Met Arg Leu Pro Gly Tyr Met Ser Arg Leu Pro Lys Leu Pro Asn
            260                 265                 270

Glu Met Leu Leu Glu Gln Ile Val Arg Leu Ile Ser Glu Ser Lys Lys
        275                 280                 285

Pro Val Leu Tyr Val Gly Gly Gly Cys Ser Gln Ser Ser Glu Glu Leu
290                 295                 300

Arg Arg Phe Val Glu Leu Thr Gly Ile Pro Val Ala Ser Thr Leu Met
305                 310                 315                 320

Gly Leu Gly Ala Phe Pro Ser Gly Asp Glu Leu Ser Leu Gln Met Leu
                325                 330                 335

Gly Met His Gly Thr Val Tyr Ala Asn Tyr Ala Val Asp Ser Ser Asp
            340                 345                 350

Leu Leu Leu Ala Phe Gly Val Arg Phe Asp Asp Arg Val Thr Gly Lys
        355                 360                 365

Leu Glu Ala Phe Ala Ser Arg Ala Lys Ile Val His Ile Asp Ile Asp
370                 375                 380

Ser Ala Glu Ile Gly Lys Asn Lys Gln Pro His Val Ser Ile Cys Ala
385                 390                 395                 400

Asp Ile Lys Leu Ala Leu Gln Gly Leu Asn Ser Ile Phe Glu Ser Lys
                405                 410                 415

Lys Gly Lys Leu Lys Leu Asp Phe Ser Ala Trp Arg Gln Glu Leu Thr
            420                 425                 430

Glu Gln Lys Val Lys Tyr Pro Leu Asn Phe Lys Thr Phe Gly Glu Ala
        435                 440                 445

Ile Pro Pro Gln Tyr Ala Ile Gln Val Leu Asp Glu Leu Thr Asn Gly
450                 455                 460

Asn Ala Ile Ile Ser Thr Gly Val Gly Gln His Gln Met Trp Ala Ala
465                 470                 475                 480
```

```
Gln His Tyr Lys Tyr Lys Lys Pro Arg Gln Trp Leu Thr Ser Gly Gly
                485                 490                 495

Leu Gly Ala Met Gly Phe Gly Leu Pro Ala Ala Ile Gly Ala Ala Val
            500                 505                 510

Gly Arg Pro Gly Glu Ile Val Val Asp Ile Asp Gly Asp Gly Ser Phe
        515                 520                 525

Ile Met Asn Val Gln Glu Leu Ala Thr Ile Lys Val Glu Asn Leu Pro
    530                 535                 540

Val Lys Ile Met Leu Leu Asn Asn Gln His Leu Gly Met Val Val Gln
545                 550                 555                 560

Trp Glu Asp Arg Phe Tyr Lys Ala Asn Arg Ala His Thr Tyr Leu Gly
                565                 570                 575

Asn Pro Ala Asn Glu Glu Glu Ile Phe Pro Asn Met Leu Lys Phe Ala
            580                 585                 590

Glu Ala Cys Gly Val Pro Ala Ala Arg Val Ser His Arg Asp Asp Leu
        595                 600                 605

Arg Ala Ala Ile Gln Lys Met Leu Asp Thr Pro Gly Pro Tyr Leu Leu
    610                 615                 620

Asp Val Ile Val Pro His Gln Glu His Val Leu Pro Met Ile Pro Ser
625                 630                 635                 640

Gly Gly Ala Phe Lys Asp Val Ile Thr Glu Gly Asp Gly Arg Arg Ser
                645                 650                 655

Tyr

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C22

<400> SEQUENCE: 11

Gly Gln Cys Arg Gly Gly Leu Ile Gly Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C17

<400> SEQUENCE: 12

Gly Gln Ser Ala Arg Arg Met Ile Gly Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C14

<400> SEQUENCE: 13
```

```
Gly Gln Val Gln Gly Gly Leu Ile Gly Thr
1               5                   10
```

<210> SEQ ID NO 14
<211> LENGTH: 657
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ALS2_C22

<400> SEQUENCE: 14

```
Met Ala Ala Ala Ser Pro Ser Pro Cys Phe Ser Lys Thr Leu Pro Pro
1               5                   10                  15

Ser Ser Ser Lys Ser Ser Thr Leu Leu Pro Lys Ser Thr Phe Thr Phe
            20                  25                  30

His Asn His Pro Lys Lys Ala Ser Pro Leu His Leu Thr His Thr Gln
        35                  40                  45

His His Ser Arg Phe Thr Val Ser Asn Val Ile Leu Ser Thr Thr Thr
50                  55                  60

His Asp Asp Val Ser Glu Pro Glu Ile Phe Val Ser Arg Phe Ala Pro
65                  70                  75                  80

Asp Glu Pro Arg Lys Gly Cys Asp Val Leu Val Glu Ala Leu Glu Arg
                85                  90                  95

Glu Gly Val Lys Asp Val Phe Ala Tyr Pro Gly Gly Ala Ser Met Glu
            100                 105                 110

Ile His Gln Ala Leu Thr Arg Ser Asn Ile Ile Arg Asn Val Leu Pro
        115                 120                 125

Arg His Glu Gln Gly Gly Val Phe Ala Ala Glu Gly Tyr Ala Arg Ala
    130                 135                 140

Thr Gly Phe Pro Gly Val Cys Ile Ala Thr Ser Gly Pro Gly Ala Thr
145                 150                 155                 160

Asn Leu Val Ser Gly Leu Ala Asp Ala Leu Leu Asp Ser Ile Pro Ile
                165                 170                 175

Val Ala Ile Thr Gly Gln Cys Arg Gly Gly Leu Ile Gly Thr Asp Ala
            180                 185                 190

Phe Gln Glu Thr Pro Ile Val Glu Val Thr Arg Ser Ile Thr Lys His
        195                 200                 205

Asn Tyr Leu Val Met Asp Val Glu Asp Ile Pro Arg Val Val Arg Glu
    210                 215                 220

Ala Phe Phe Leu Ala Lys Ser Gly Arg Pro Gly Pro Val Leu Ile Asp
225                 230                 235                 240

Val Pro Lys Asp Ile Gln Gln Gln Leu Val Ile Pro Asn Trp Asp Gln
                245                 250                 255

Pro Met Arg Leu Pro Gly Tyr Met Ser Arg Leu Pro Lys Leu Pro Asn
            260                 265                 270

Glu Met Leu Leu Glu Gln Ile Val Arg Leu Ile Ser Glu Ser Lys Lys
        275                 280                 285

Pro Val Leu Tyr Val Gly Gly Cys Ser Gln Ser Ser Glu Glu Leu
    290                 295                 300

Arg Arg Phe Val Glu Leu Thr Gly Ile Pro Val Ala Ser Thr Leu Met
305                 310                 315                 320

Gly Leu Gly Ala Phe Pro Ser Gly Asp Glu Leu Ser Leu Gln Met Leu
                325                 330                 335
```

Gly Met His Gly Thr Val Tyr Ala Asn Tyr Ala Val Asp Ser Ser Asp
            340                 345                 350

Leu Leu Leu Ala Phe Gly Val Arg Phe Asp Asp Arg Val Thr Gly Lys
            355                 360                 365

Leu Glu Ala Phe Ala Ser Arg Ala Lys Ile Val His Ile Asp Ile Asp
370                 375                 380

Ser Ala Glu Ile Gly Lys Asn Lys Gln Pro His Val Ser Ile Cys Ala
385                 390                 395                 400

Asp Ile Lys Leu Ala Leu Gln Gly Leu Asn Ser Ile Phe Glu Ser Lys
            405                 410                 415

Lys Gly Lys Leu Lys Leu Asp Phe Ser Ala Trp Arg Gln Glu Leu Thr
            420                 425                 430

Glu Gln Lys Val Lys Tyr Pro Leu Asn Phe Lys Thr Phe Gly Glu Ala
            435                 440                 445

Ile Pro Pro Gln Tyr Ala Ile Gln Val Leu Asp Glu Leu Thr Asn Gly
            450                 455                 460

Asn Ala Ile Ile Ser Thr Gly Val Gly Gln His Gln Met Trp Ala Ala
465                 470                 475                 480

Gln His Tyr Lys Tyr Lys Lys Pro Arg Gln Trp Leu Thr Ser Gly Gly
            485                 490                 495

Leu Gly Ala Met Gly Phe Gly Leu Pro Ala Ala Ile Gly Ala Ala Val
            500                 505                 510

Gly Arg Pro Gly Glu Ile Val Val Asp Ile Asp Gly Asp Gly Ser Phe
            515                 520                 525

Ile Met Asn Val Gln Glu Leu Ala Thr Ile Lys Val Glu Asn Leu Pro
530                 535                 540

Val Lys Ile Met Leu Leu Asn Asn Gln His Leu Gly Met Val Val Gln
545                 550                 555                 560

Trp Glu Asp Arg Phe Tyr Lys Ala Asn Arg Ala His Thr Tyr Leu Gly
            565                 570                 575

Asn Pro Ala Asn Glu Glu Glu Ile Phe Pro Asn Met Leu Lys Phe Ala
            580                 585                 590

Glu Ala Cys Gly Val Pro Ala Ala Arg Val Ser His Arg Asp Asp Leu
            595                 600                 605

Arg Ala Ala Ile Gln Lys Met Leu Asp Thr Pro Gly Pro Tyr Leu Leu
610                 615                 620

Asp Val Ile Val Pro His Gln Glu His Val Leu Pro Met Ile Pro Ser
625                 630                 635                 640

Gly Gly Ala Phe Lys Asp Val Ile Thr Glu Gly Asp Gly Arg Arg Ser
            645                 650                 655

Tyr

<210> SEQ ID NO 15
<211> LENGTH: 657
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ALS2_C17

<400> SEQUENCE: 15

Met Ala Ala Ala Ser Pro Ser Pro Cys Phe Ser Lys Thr Leu Pro Pro
1               5                   10                  15

```
Ser Ser Ser Lys Ser Ser Thr Leu Leu Pro Lys Ser Thr Phe Thr Phe
            20              25              30

His Asn His Pro Lys Lys Ala Ser Pro Leu His Leu Thr His Thr Gln
            35              40              45

His His Ser Arg Phe Thr Val Ser Asn Val Ile Leu Ser Thr Thr Thr
50              55              60

His Asp Asp Val Ser Glu Pro Glu Ile Phe Val Ser Arg Phe Ala Pro
65              70              75              80

Asp Glu Pro Arg Lys Gly Cys Asp Val Leu Val Glu Ala Leu Glu Arg
            85              90              95

Glu Gly Val Lys Asp Val Phe Ala Tyr Pro Gly Gly Ala Ser Met Glu
            100             105             110

Ile His Gln Ala Leu Thr Arg Ser Asn Ile Ile Arg Asn Val Leu Pro
            115             120             125

Arg His Glu Gln Gly Gly Val Phe Ala Ala Glu Gly Tyr Ala Arg Ala
130             135             140

Thr Gly Phe Pro Gly Val Cys Ile Ala Thr Ser Gly Pro Gly Ala Thr
145             150             155             160

Asn Leu Val Ser Gly Leu Ala Asp Ala Leu Leu Asp Ser Ile Pro Ile
            165             170             175

Val Ala Ile Thr Gly Gln Ser Ala Arg Arg Met Ile Gly Thr Asp Ala
            180             185             190

Phe Gln Glu Thr Pro Ile Val Glu Val Thr Arg Ser Ile Thr Lys His
            195             200             205

Asn Tyr Leu Val Met Asp Val Glu Asp Ile Pro Arg Val Val Arg Glu
210             215             220

Ala Phe Phe Leu Ala Lys Ser Gly Arg Pro Gly Pro Val Leu Ile Asp
225             230             235             240

Val Pro Lys Asp Ile Gln Gln Gln Leu Val Ile Pro Asn Trp Asp Gln
            245             250             255

Pro Met Arg Leu Pro Gly Tyr Met Ser Arg Leu Pro Lys Leu Pro Asn
            260             265             270

Glu Met Leu Leu Glu Gln Ile Val Arg Leu Ile Ser Glu Ser Lys Lys
            275             280             285

Pro Val Leu Tyr Val Gly Gly Gly Cys Ser Gln Ser Ser Glu Glu Leu
            290             295             300

Arg Arg Phe Val Glu Leu Thr Gly Ile Pro Val Ala Ser Thr Leu Met
305             310             315             320

Gly Leu Gly Ala Phe Pro Ser Gly Asp Glu Leu Ser Leu Gln Met Leu
            325             330             335

Gly Met His Gly Thr Val Tyr Ala Asn Tyr Ala Val Asp Ser Ser Asp
            340             345             350

Leu Leu Leu Ala Phe Gly Val Arg Phe Asp Asp Arg Val Thr Gly Lys
            355             360             365

Leu Glu Ala Phe Ala Ser Arg Ala Lys Ile Val His Ile Asp Ile Asp
            370             375             380

Ser Ala Glu Ile Gly Lys Asn Lys Gln Pro His Val Ser Ile Cys Ala
385             390             395             400

Asp Ile Lys Leu Ala Leu Gln Gly Leu Asn Ser Ile Phe Glu Ser Lys
            405             410             415

Lys Gly Lys Leu Lys Leu Asp Phe Ser Ala Trp Arg Gln Glu Leu Thr
            420             425             430

Glu Gln Lys Val Lys Tyr Pro Leu Asn Phe Lys Thr Phe Gly Glu Ala
```

-continued

```
                435                 440                 445
Ile Pro Pro Gln Tyr Ala Ile Gln Val Leu Asp Glu Leu Thr Asn Gly
    450                 455                 460

Asn Ala Ile Ile Ser Thr Gly Val Gly Gln His Gln Met Trp Ala Ala
465                 470                 475                 480

Gln His Tyr Lys Tyr Lys Lys Pro Arg Gln Trp Leu Thr Ser Gly Gly
                485                 490                 495

Leu Gly Ala Met Gly Phe Gly Leu Pro Ala Ala Ile Gly Ala Ala Val
            500                 505                 510

Gly Arg Pro Gly Glu Ile Val Val Asp Ile Asp Gly Asp Gly Ser Phe
        515                 520                 525

Ile Met Asn Val Gln Glu Leu Ala Thr Ile Lys Val Glu Asn Leu Pro
    530                 535                 540

Val Lys Ile Met Leu Leu Asn Asn Gln His Leu Gly Met Val Val Gln
545                 550                 555                 560

Trp Glu Asp Arg Phe Tyr Lys Ala Asn Arg Ala His Thr Tyr Leu Gly
                565                 570                 575

Asn Pro Ala Asn Glu Glu Glu Ile Phe Pro Asn Met Leu Lys Phe Ala
            580                 585                 590

Glu Ala Cys Gly Val Pro Ala Ala Arg Val Ser His Arg Asp Asp Leu
        595                 600                 605

Arg Ala Ala Ile Gln Lys Met Leu Asp Thr Pro Gly Pro Tyr Leu Leu
    610                 615                 620

Asp Val Ile Val Pro His Gln Glu His Val Leu Pro Met Ile Pro Ser
625                 630                 635                 640

Gly Gly Ala Phe Lys Asp Val Ile Thr Glu Gly Asp Gly Arg Arg Ser
                645                 650                 655

Tyr

<210> SEQ ID NO 16
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ALS1_C14

<400> SEQUENCE: 16

Met Ala Ala Ala Ser Pro Ser Pro Cys Phe Ser Lys Thr Leu Pro
1               5                   10                  15

Pro Ser Ser Ser Lys Ser Ser Thr Ile Leu Pro Arg Ser Thr Phe Ser
                20                  25                  30

Phe His Asn His Pro Gln Lys Ala Ser Pro Leu His Leu Ile His Ala
            35                  40                  45

Gln His Asn Arg Arg Gly Phe Ala Val Ala Asn Val Val Ile Ser Thr
        50                  55                  60

Thr Thr His Asn Asp Val Ser Glu Pro Glu Thr Phe Val Ser Arg Phe
65                  70                  75                  80

Ala Pro Asp Glu Pro Arg Lys Gly Cys Asp Val Leu Val Glu Ala Leu
                85                  90                  95

Glu Arg Glu Gly Val Thr Asp Val Phe Ala Tyr Pro Gly Gly Ala Ser
            100                 105                 110

Met Glu Ile His Gln Ala Leu Thr Arg Ser Asn Ile Ile Arg Asn Val
        115                 120                 125
```

```
Leu Pro Arg His Glu Gln Gly Val Phe Ala Ala Glu Gly Tyr Ala
    130                 135                 140

Arg Ala Thr Gly Phe Pro Gly Val Cys Ile Ala Thr Ser Gly Pro Gly
145                 150                 155                 160

Ala Thr Asn Leu Val Ser Gly Leu Ala Asp Ala Leu Leu Asp Ser Ile
                165                 170                 175

Pro Ile Val Ala Ile Thr Gly Gln Val Gln Gly Leu Ile Gly Thr
            180                 185                 190

Asp Ala Phe Gln Glu Thr Pro Ile Val Glu Val Thr Arg Ser Ile Thr
                195                 200                 205

Lys His Asn Tyr Leu Val Met Asp Val Glu Asp Ile Pro Arg Val Val
    210                 215                 220

Arg Glu Ala Phe Phe Leu Ala Lys Ser Gly Arg Pro Gly Pro Val Leu
225                 230                 235                 240

Ile Asp Val Pro Lys Asp Ile Gln Gln Gln Leu Val Ile Pro Asn Trp
                245                 250                 255

Asp Gln Pro Met Arg Leu Pro Gly Tyr Met Ser Arg Leu Pro Lys Leu
                260                 265                 270

Pro Asn Glu Met Leu Leu Glu Gln Ile Val Arg Leu Ile Ser Glu Ser
            275                 280                 285

Lys Lys Pro Val Leu Tyr Val Gly Gly Gly Cys Ser Gln Ser Ser Glu
    290                 295                 300

Glu Leu Arg Arg Phe Val Glu Leu Thr Gly Ile Pro Val Ala Ser Thr
305                 310                 315                 320

Leu Met Gly Leu Gly Ala Phe Pro Thr Gly Asp Glu Leu Ser Leu Gln
                325                 330                 335

Met Leu Gly Met His Gly Thr Val Tyr Ala Asn Tyr Ala Val Asp Ser
                340                 345                 350

Ser Asp Leu Leu Leu Ala Phe Gly Val Arg Phe Asp Asp Arg Val Thr
        355                 360                 365

Gly Lys Leu Glu Ala Phe Ala Ser Arg Ala Lys Ile Val His Ile Asp
    370                 375                 380

Ile Asp Ser Ala Glu Ile Gly Lys Asn Lys Gln Pro His Val Ser Ile
385                 390                 395                 400

Cys Ala Asp Ile Lys Leu Ala Leu Gln Gly Leu Asn Ser Ile Leu Glu
                405                 410                 415

Gly Lys Glu Gly Lys Met Lys Leu Asp Phe Ser Ala Trp Arg Gln Glu
                420                 425                 430

Leu Thr Glu Gln Lys Met Lys Tyr Pro Leu Asn Phe Lys Thr Phe Gly
        435                 440                 445

Asp Ala Ile Pro Pro Gln Tyr Ala Ile Gln Val Leu Asp Glu Leu Thr
    450                 455                 460

Asn Gly Asn Ala Ile Ile Ser Thr Gly Val Gly Gln His Gln Met Trp
465                 470                 475                 480

Ala Ala Gln Tyr Tyr Lys Tyr Lys Lys Pro Arg Gln Trp Leu Thr Ser
                485                 490                 495

Gly Gly Leu Gly Ala Met Gly Phe Gly Leu Pro Ala Ala Ile Gly Ala
                500                 505                 510

Ala Val Gly Arg Pro Gly Glu Ile Val Val Asp Ile Asp Gly Asp Gly
            515                 520                 525

Ser Phe Ile Met Asn Val Gln Glu Leu Ala Thr Ile Lys Val Glu Asn
    530                 535                 540
```

```
Leu Pro Val Lys Ile Met Leu Leu Asn Asn Gln His Leu Gly Met Val
545                 550                 555                 560

Val Gln Trp Glu Asp Arg Phe Tyr Lys Ala Asn Arg Ala His Thr Tyr
            565                 570                 575

Leu Gly Asp Pro Ser Asn Glu Glu Ile Phe Pro Asn Met Leu Lys
        580                 585                 590

Phe Ala Glu Ala Cys Gly Val Pro Ala Ala Arg Val Ser His Arg Asp
        595                 600                 605

Asp Leu Arg Ala Ala Ile Gln Lys Met Leu Asp Thr Pro Gly Pro Tyr
    610                 615                 620

Leu Leu Asp Val Ile Val Pro His Gln Glu His Val Leu Pro Met Ile
625                 630                 635                 640

Pro Ser Gly Gly Ala Phe Lys Asp Val Ile Thr Glu Gly Asp Gly Arg
                645                 650                 655

Cys Ser Tyr

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 WT part

<400> SEQUENCE: 17
ggtcaagtgc caaggaggat gatt                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 WT part

<400> SEQUENCE: 18
ggtcaagtgc cgaggaggat gatt                                          24

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ALS WT1-2 part

<400> SEQUENCE: 19

Gly Gln Val Pro Arg Arg Met Ile Gly Thr
1               5                   10

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1_WT part extended
```

<400> SEQUENCE: 20
gctattacag gtcaagtgcc aaggaggatg attggtact                                   39

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2_WT part extended

<400> SEQUENCE: 21
gctattaccg gtcaagtgcc gaggaggatg attggtact                                   39

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ALS 1-2 part extended

<400> SEQUENCE: 22

Ala Ile Thr Gly Gln Val Pro Arg Arg Met Ile Gly Thr
1               5                   10

<210> SEQ ID NO 23
<211> LENGTH: 5126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Promotor/Cas9
<220> FEATURE:
<221> NAME/KEY: misc_feature
<222> LOCATION: (1)..(972)
<223> OTHER INFORMATION: promoter
<220> FEATURE:
<221> NAME/KEY: misc_feature
<222> LOCATION: (987)..(5126)
<223> OTHER INFORMATION: ORF

<400> SEQUENCE: 23
aaaaattacg gatatgaata taggcatatc cgtatccgaa ttatccgttt gacagctagc    60
aacgattgta caattgcttc tttaaaaaag gaagaaagaa agaaagaaaa gaatcaacat   120
cagcgttaac aaacggcccc gttacggccc aaacggtcat atagagtaac ggcgttaagc   180
gttgaaagac tcctatcgaa atacgtaacc gcaaacgtgt catagtcaga tcccctcttc   240
cttcaccgcc tcaaacacaa aaataatctt ctacagccta tatataacc ccccccttct    300 atctctcctt tctcacaatt catcatcttt ctttctctac ccccaatttt aagaaatcct   360
ctcttctcct cttcattttc aaggtaaatc tctctctctc tctctctctc tgttattcct   420
tgttttaatt aggtatgtat tattgctagt ttgttaatct gcttatctta tgtatgcctt   480
atgtgaatat ctttatcttg ttcatctcat ccgtttagaa gctataaatt tgttgatttg   540
actgtgtatc tacacgtggt tatgttata tctaatcaga tatgaatttc ttcatattgt    600
tgcgtttgtg tgtaccaatc cgaaatcgtt gatttttttc atttaatcgt gtagctaatt   660

```
gtacgtatac atatggatct acgtatcaat tgttcatctg tttgtgtttg tatgtataca      720
gatctgaaaa catcacttct ctcatctgat tgtgttgtta catacataga tatagatctg      780
ttatatcatt ttttttatta attgtgtata tatatatgtg catagatctg gattacatga      840
ttgtgattat ttacatgatt ttgttattta cgtatgtata tatgtagatc tggactttt       900 ggagttgttg acttgattgt atttgtgtgt gtatatgtgt gttctgatct tgatatgtta      960
tgtatgtgca gcgaattcgg cgcgccatgg ataagaagta ctctatcgga ctcgatatcg     1020
gaactaactc tgtgggatgg gctgtgatca ccgatgagta caaggtgcca tctaagaagt     1080
tcaaggttct cggaaacacc gataggcact ctatcaagaa aaaccttatc ggtgctctcc     1140
tcttcgattc tggtgaaact gctgaggcta ccagactcaa gagaaccgct agaagaaggt     1200
acaccagaag aaagaacagg atctgctacc tccaagagat cttctctaac gagatggcta     1260
aagtggatga ttcattcttc cacaggctcg aagagtcatt cctcgtggaa gaagataaga     1320
agcacgagag gcaccctatc ttcggaaaca tcgttgatga ggtggcatac cacgagaagt     1380
accctactat ctaccacctc agaaagaagc tcgttgattc tactgataag gctgatctca     1440
ggctcatcta cctcgctctc gctcacatga tcaagttcag aggacacttc ctcatcgagg     1500
gtgatctcaa ccctgataac tctgatgtgg ataagttgtt catccagctc gtgcagacct     1560
acaaccagct tttcgaagag aaccctatca cgcttcagg tgtggatgct aaggctatcc     1620
tctctgctag gctctctaag tcaagaaggc ttgagaacct cattgctcag ctccctggtg     1680
agaagaagaa cggacttttc ggaaacttga tcgctctctc tctcggactc accctaact      1740 tcaagtctaa cttcgatctc gctgaggatg caaagctcca gctctcaaag gatacctacg     1800
atgatgatct cgataacctc ctcgctcaga tcggagatca gtacgctgat ttgttcctcg     1860
ctgctaagaa cctctctgat gctatcctcc tcagtgatat cctcagagtg aacaccgaga     1920
tcaccaaggc tccactctca gcttctatga tcaagagata cgatgagcac caccaggatc     1980
tcacacttct caaggctctt gttagacagc agctcccaga aagtacaaa gagattttct      2040 tcgatcagtc taagaacgga tacgctggtt acatcgatgg tggtgcatct caagaagagt     2100
tctacaagtt catcaagcct atcctcgaga agatggatgg aaccgaggaa ctcctcgtga     2160
agctcaatag agaggatctt ctcagaaagc agaggacctt cgataacgga tctatccctc     2220
atcagatcca cctcggagag ttgcacgcta tccttagaag gcaagaggat ttctacccat     2280
tcctcaagga taacagggaa aagattgaga agattctcac cttcagaatc ccttactacg     2340 tgggaccttct cgctagagga aactcaagat tcgcttggat gaccagaaag tctgaggaaa     2400
ccatcacccc ttggaacttc gaagaggtgg tggataaggg tgctagtgct cagtctttca     2460
tcgagaggat gaccaacttc gataagaacc ttccaaacga aaggtgctc cctaagcact      2520 ctttgctcta cgagtacttc accgtgtaca acagttgac caaggttaag tacgtgaccg      2580
agggaatgag gaagcctgct ttttttgtcag gtgagcaaaa aaaggctatc gttgatctct     2640
tgttcaagac caacagaaag gtgaccgtga agcagctcaa agaggattac ttcaagaaaa     2700
tcgagtgctt cgattcagtt gagatttctg gtgttgagga taggttcaac gcatctctcg     2760
gaacctacca cgatctcctc aagatcatta aggataagga tttcttggat aacgaggaaa     2820
acgaggatat cttggaggat atcgttctta ccctcaccct ctttgaagat agagagatga     2880
ttgaagaaag gctcaagacc tacgctcatc tcttcgatga taaggtgatg aagcagttga     2940
agagaagaag atacactggt tgggaaggc tctcaagaaa gctcattaac ggaatcaggg       3000
ataagcagtc tggaaagaca atccttgatt tcctcaagtc tgatggattc gctaacagaa     3060
```

```
acttcatgca gctcatccac gatgattctc tcacctttaa agaggatatc cagaaggctc    3120
aggtttcagg acagggtgat agtctccatg agcatatcgc taacctcgct ggatctcctg    3180
caatcaagaa gggaatcctc cagactgtga aggttgtgga tgagttggtg aaggtgatgg    3240
gaaggcataa gcctgagaac atcgtgatcg aaatggctag agagaaccag accactcaga    3300
agggacagaa gaactctagg gaaaggatga gaggatcga ggaaggtatc aaagagcttg    3360
gatctcagat cctcaaagag caccctgttg agaacactca gctccagaat gagaagctct    3420
acctctacta cctccagaac ggaagggata tgtatgtgga tcaagagttg gatatcaaca    3480
ggctctctga ttacgatgtt gatcatatcg tgccacagtc attcttgaag gatgattcta    3540
tcgataacaa ggtgctcacc aggtctgata gaacagggg taagagtgat aacgtgccaa    3600
gtgaagaggt tgtgaagaaa atgaagaact attggaggca gctcctcaac gctaagctca    3660
tcactcagag aaagttcgat aacttgacta aggctgagag gggaggactc tctgaattgg    3720
ataaggcagg attcatcaag aggcagcttg tggaaaccag gcagatcact aagcacgttg    3780
cacagatcct cgattctagg atgaacacca agtacgatga aacgataag ttgatcaggg    3840 aagtgaaggt tatcaccctc aagtcaaagc tcgtgtctga tttcagaaag gatttccaat    3900
tctacaaggt gagggaaatc aacaactacc accacgctca cgatgcttac cttaacgctg    3960
ttgttggaac cgctctcatc aagaagtatc ctaagctcga gtcagagttc gtgtacggtg    4020
attacaaggt gtacgatgtg aggaagatga tcgctaagtc tgagcaagag atcggaaagg    4080
ctaccgctaa gtatttcttc tactctaaca tcatgaattt cttcaagacc gagattaccc    4140
tcgctaacgg tgagatcaga aagaggccac tcatcgagac aaacggtgaa acaggtgaga    4200
tcgtgtggga taagggaagg gatttcgcta ccgttagaaa ggtgctctct atgccacagg    4260
tgaacatcgt taagaaaacc gaggtgcaga ccggtggatt ctctaaagag tctatcctcc    4320
ctaagaggaa ctctgataag ctcattgcta ggaagaagga ttgggaccct aagaaatacg    4380
gtggtttcga ttctcctacc gtggcttact ctgttctcgt tgtggctaag gttgagaagg    4440
gaaagagtaa gaagctcaag tctgttaagg aacttctcgg aatcactatc atggaaaggt    4500
catctttcga gaagaaccca atcgatttcc tcgaggctaa gggatacaaa gaggttaaga    4560
aggatctcat catcaagctc ccaaagtact cactcttcga actcgagaac ggtagaaaga    4620
ggatgctcgc ttctgctggt gagcttcaaa agggaaacga gcttgctctc ccatctaagt    4680
acgttaactt tctttacctc gcttctcact acgagaagtt gaagggatct ccagaagata    4740
acgagcagaa gcaactttc gttgagcagc acaagcacta cttggatgag atcatcgagc    4800
agatctctga gttctctaaa agggtgatcc tcgctgatgc aaacctcgat aaggtgttgt    4860
ctgcttacaa caagcacaga gataagccta tcagggaaca ggcagagaac atcatccatc    4920 tcttcacccct taccaacctc ggtgctcctg ctgctttcaa gtacttcgat acaaccatcg    4980
ataggaagag atacacctct accaaagaag tgctcgatgc taccctcatc catcagtcta    5040
tcactggact ctacgagact aggatcgatc tctcacagct cggtggtgat tcaagggctg    5100
atcctaagaa gaagaggaag gtttga                                          5126
```

<210> SEQ ID NO 24
<211> LENGTH: 1379
<212> TYPE: PRT
<213> ORGANISM: Artificial Sequence
<220> FEATURE:
<223> OTHER INFORMATION: Description of Artificial Sequence: Synthetic polypeptide -continued

<220> FEATURE:
<223> OTHER INFORMATION: CAS9

<400> SEQUENCE: 24

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400
```

```
Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815
```

-continued

Gln Asn Gly Arg Asp Met Tyr Val Asp Glu Leu Asp Ile Asn Arg
                820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
    995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val

```
                    1220                 1225                 1230

Asn  Phe  Leu  Tyr  Leu  Ala  Ser  His  Tyr  Glu  Lys  Leu  Lys  Gly  Ser
               1235                 1240                 1245

Pro  Glu  Asp  Asn  Glu  Gln  Lys  Gln  Leu  Phe  Val  Glu  Gln  His  Lys
     1250                 1255                 1260

His  Tyr  Leu  Asp  Glu  Ile  Ile  Glu  Gln  Ile  Ser  Glu  Phe  Ser  Lys
     1265                 1270                 1275

Arg  Val  Ile  Leu  Ala  Asp  Ala  Asn  Leu  Asp  Lys  Val  Leu  Ser  Ala
     1280                 1285                 1290

Tyr  Asn  Lys  His  Arg  Asp  Lys  Pro  Ile  Arg  Glu  Gln  Ala  Glu  Asn
     1295                 1300                 1305

Ile  Ile  His  Leu  Phe  Thr  Leu  Thr  Asn  Leu  Gly  Ala  Pro  Ala  Ala
     1310                 1315                 1320

Phe  Lys  Tyr  Phe  Asp  Thr  Thr  Ile  Asp  Arg  Lys  Arg  Tyr  Thr  Ser
     1325                 1330                 1335

Thr  Lys  Glu  Val  Leu  Asp  Ala  Thr  Leu  Ile  His  Gln  Ser  Ile  Thr
     1340                 1345                 1350

Gly  Leu  Tyr  Glu  Thr  Arg  Ile  Asp  Leu  Ser  Gln  Leu  Gly  Gly  Asp
     1355                 1360                 1365

Ser  Arg  Ala  Asp  Pro  Lys  Lys  Lys  Arg  Lys  Val
     1370                 1375
```

<210> SEQ ID NO 25
<211> LENGTH: 221
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: KG10177

<400> SEQUENCE: 25

```
ggagtgatca aaagtcccac atcgatcagg tgatatatag cagcttagtt tatataatga    60
tagagtcgac atagcgattg caagtgccga ggaggatgat gttttagagc tagaaatagc   120
aagttaaaat aaggctagtc cgttatcaac ttgaaaaagt ggcaccgagt cggtgctttt   180
tttctagacc cagctttctt gtacaaagtt ggcattacgc t                       221
```

<210> SEQ ID NO 26
<211> LENGTH: 221
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: KG10190

<400> SEQUENCE: 26

```
ggagtgatca aaagtcccac atcgatcagg tgatatatag cagcttagtt tatataatga    60
tagagtcgac atagcgattg catcctcctc ggcacttgac gttttagagc tagaaatagc   120
aagttaaaat aaggctagtc cgttatcaac ttgaaaaagt ggcaccgagt cggtgctttt   180
tttctagacc cagctttctt gtacaaagtt ggcattacgc t                       221
```

<210> SEQ ID NO 27
<211> LENGTH: 221
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: KG10191

<400> SEQUENCE: 27
ggagtgatca aaagtcccac atcgatcagg tgatatatag cagcttagtt tatataatga    60
tagagtcgac atagcgattg ttaccggtca agtgccgagg gttttagagc tagaaatagc   120
aagttaaaat aaggctagtc cgttatcaac ttgaaaaagt ggcaccgagt cggtgctttt   180
tttctagacc cagctttctt gtacaaagtt ggcattacgc t                       221

<210> SEQ ID NO 28
<211> LENGTH: 644
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: KG10240

<400> SEQUENCE: 28
ggagtgatca aaagtcccac atcgatcagg tgatatatag cagcttagtt tatataatga    60
tagagtcgac atagcgattg aacaaagcac cagtggtcta gtggtagaat agtaccctgc   120
cacggtacag acccgggttc gattcccggc tggtgcacaa gtgccgagga ggatgatgtt   180
ttagagctag aaatagcaag ttaaaataag gctagtccgt tatcaacttg aaaaagtggc   240
accgagtcgg tgcaacaaag caccagtggt ctagtggtag aatagtaccc tgccacggta   300
cagacccggg ttcgattccc ggctggtgca catcctcctc ggcacttgac gttttagagc   360
tagaaatagc aagttaaaat aaggctagtc cgttatcaac ttgaaaaagt ggcaccgagt   420
cggtgcaaca agcaccagt ggtctagtgg tagaatagta ccctgccacg gtacagaccc   480
gggttcgatt cccggctggt gcattaccgg tcaagtgccg agggttttag agctagaaat   540
agcaagttaa aataaggcta gtccgttatc aacttgaaaa agtggcaccg agtcggtgct   600 tttttctag acccagcttt cttgtacaaa gttggcatta cgct                    644

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 fig3

<400> SEQUENCE: 29
attaccggtc aagtgccgag gaggatgatt gg                                  32

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA1

<400> SEQUENCE: 30
attaccggtc aagtgccgag gaggattgat tgg                33

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA1a

<400> SEQUENCE: 31
attaccggtc aagtgccggg atgattgg                28

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA1b

<400> SEQUENCE: 32
attaccggtc aagtgccgag gatgattgg                29

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA1c

<400> SEQUENCE: 33
attaccggtc aagtgccgag gagattgg                28

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA2

<400> SEQUENCE: 34
attaccggtc aaagtgccga ggaggatgat tgg                33

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA2a

<400> SEQUENCE: 35
attaccggtc agtgccgagg aggatgattg g                31

<210> SEQ ID NO 36

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA2b

<400> SEQUENCE: 36
attaccggtc gtgccgagga ggatgattgg                               30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA2c

<400> SEQUENCE: 37
attaccggtc atgccgagga ggatgattgg                               30

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA3

<400> SEQUENCE: 38
attaccggtc aagtgccagg aggatgattg g                             31

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA3a

<400> SEQUENCE: 39
attaccggtc aaggaggatg attgg                                    25

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sgRNA3b

<400> SEQUENCE: 40
attaccggtc aagtgccgca ggaggatgat tgg                           33

<210> SEQ ID NO 41
<211> LENGTH: 33
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: ALS2 sgRNA3c

<400> SEQUENCE: 41
attaccggtc aagtgccgta ggaggatgat tgg                          33

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sg1+2+3

<400> SEQUENCE: 42
attaccggtc aagtgccggg atgattgg                                28

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sg1+2+3a

<400> SEQUENCE: 43
attaccggtc aagtgccagg aggatgattg g                            31

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sg1+2+3b

<400> SEQUENCE: 44
attaccggtc aagtgccgag attgg                                   25

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sg1+2+3c

<400> SEQUENCE: 45
attaccggtc gccgaggagg attgattgg                               29

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sg1+2+3d
```

```
<400> SEQUENCE: 46
attaccggtc aagtgccgta ggagggattg g                              31

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sg1+2+3e

<400> SEQUENCE: 47
attaccggtc aagtgccagg aggagattgg                                30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sg1+2+3f

<400> SEQUENCE: 48
attaccggtc tgccgaggag gattgattgg                                30

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS2 sg1+2+3g

<400> SEQUENCE: 49
attaccggtc agccgaggag gattgg                                    26

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 fig3

<400> SEQUENCE: 50
attacaggtc aagtgccaag gaggatgatt gg                             32

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sgRNA1

<400> SEQUENCE: 51
attacaggtc aagtgccaag gaggatattg g                              31
```

```
<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sgRNA1a

<400> SEQUENCE: 52
attacaggtc aagtgccaag gaggattgat tgg                                33

<210> SEQ ID NO 53
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sgRNA1b

<400> SEQUENCE: 53
attacaggtc aagtgccaag gaggattgg                                     29

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sgRNA1c

<400> SEQUENCE: 54
attacaggtc aagtgccaag gagggattgg                                    30

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sgRNA3

<400> SEQUENCE: 55
attacaggtc aagtgccaaa ggaggatgat tgg                                33

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sgRNA3a

<400> SEQUENCE: 56
attacaggtc aaggaggatg attgg                                         25

<210> SEQ ID NO 57
<211> LENGTH: 31
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sgRNA3b

<400> SEQUENCE: 57
attacaggtc aagtgccagg aggatgattg g                              31

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sgRNA3c

<400> SEQUENCE: 58
attacaggtc aagtaggagg atgattgg                                  28

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sg1+2+3

<400> SEQUENCE: 59
attacaggtc aagtgccagg aggatgattg g                              31

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sg1+2+3a

<400> SEQUENCE: 60
attacaggtc aagtgccaag gatgattgg                                 29

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sg1+2+3b

<400> SEQUENCE: 61
attacaggtc aagtgccaag gagattgg                                  28

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: ALS1 sg1+2+3c

<400> SEQUENCE: 62
attacaggtc aagtgccaag gaggattgat tgg                                    33

<210> SEQ ID NO 63
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sg1+2+3d

<400> SEQUENCE: 63
attacaggtc aagtgccaaa ggaggattga ttgg                                   34

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sg1+2+3e

<400> SEQUENCE: 64
attacaggtc aagtgccagg aggattgatt gg                                     32

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sg1+2+3f

<400> SEQUENCE: 65
attacaggtc aagtgccagg agggattgg                                         29

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ALS1 sg1+2+3g

<400> SEQUENCE: 66
attacaggtc aagtaggagg attgattgg                                         29

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer ALS1 Fw
```

<400> SEQUENCE: 67
tggcgctcat cacttctt                                                        18

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer ALS1 Rev

<400> SEQUENCE: 68
cgttacctca acaataggcg tttcct                                               26

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer ALS2 Fw

<400> SEQUENCE: 69
cacctcattt tcatggccct                                                      20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer ALS2 Rev

<400> SEQUENCE: 70
agccttcacg aacaacccta                                                      20

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gln Cys Arg Gly Gly Leu Ile Gly Thr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gln Ser Ala Arg Arg Met Ile Gly Thr
1               5                   10

<210> SEQ ID NO 73

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Gln Val Pro Gly Gly Leu Met Ile Gly Thr
1               5                   10

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Arg Arg Gly Gly Leu Ile Gly Thr
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Gln Val Gln Gly Gly Leu Ile Gly Thr
1               5                   10
```